(12) United States Patent
Rast et al.

(10) Patent No.: US 11,433,029 B2
(45) Date of Patent: ***Sep. 6, 2022

(54) FORMULATION OF AN ANTIBODY AND USE THEREOF

(71) Applicant: TAKEDA PHARMACEUTICAL COMPANY LIMITED, Osaka (JP)

(72) Inventors: Markus Rast, Radolfzell (DE);
Wolfgang Ise, Constance (DE);
Gerhard Becker, Allensbach (DE);
Peter Skufca, Stockach (DE); Henning Gieseler, Rottendorf (DE)

(73) Assignee: TAKEDA PHARMACEUTICAL COMPANY LIMITED, Osaka (JP)

( * ) Notice: Subject to any disclaimer, the term of this patent is extended or adjusted under 35 U.S.C. 154(b) by 61 days.

This patent is subject to a terminal disclaimer.

(21) Appl. No.: 14/773,478

(22) PCT Filed: Mar. 17, 2014

(86) PCT No.: PCT/EP2014/055279
§ 371 (c)(1),
(2) Date: Sep. 8, 2015

(87) PCT Pub. No.: WO2014/140361
PCT Pub. Date: Sep. 18, 2014

(65) Prior Publication Data
US 2016/0022585 A1    Jan. 28, 2016

Related U.S. Application Data

(60) Provisional application No. 61/787,225, filed on Mar. 15, 2013.

(30) Foreign Application Priority Data

Mar. 15, 2013  (EP) .................................. 13159325

(51) Int. Cl.
*A61K 39/395* (2006.01)
*A61K 9/19* (2006.01)
*C07K 16/28* (2006.01)

(52) U.S. Cl.
CPC ............ *A61K 9/19* (2013.01); *C07K 16/2887* (2013.01); *C07K 2317/24* (2013.01)

(58) Field of Classification Search
None
See application file for complete search history.

(56) References Cited

U.S. PATENT DOCUMENTS

| | | | | |
|---|---|---|---|---|
| 2001/0014326 A1* | 8/2001 | Andya | ............ | A61K 39/39591 424/130.1 |
| 2006/0088523 A1* | 4/2006 | Andya | .................. | C07K 16/32 424/133.1 |
| 2011/0236383 A1 | 9/2011 | Andya et al. | | |

FOREIGN PATENT DOCUMENTS

| | | |
|---|---|---|
| EP | 2 727 602 A1 | 5/2014 |
| WO | 97/04801 A1 | 2/1997 |
| WO | 03/009817 A2 | 2/2003 |
| WO | 03/009817 A3 | 2/2003 |
| WO | 2007/014073 A2 | 2/2007 |
| WO | 2008/157409 A1 | 12/2008 |
| WO | 2009/080541 A1 | 7/2009 |
| WO | 2010/011697 A1 | 1/2010 |
| WO | 2010/017296 A1 | 2/2010 |
| WO | 2010/148321 A1 | 12/2010 |
| WO | 2010/148337 A1 | 12/2010 |
| WO | 2011/017070 A1 | 2/2011 |
| WO | 2011/029892 A2 | 3/2011 |

OTHER PUBLICATIONS

Breen, et al, "Effect of Moisture on the Stability of a Lyophilized Humanized Monoclonal Antibody Formulation", Pharmaceutical Research, vol. 18, No. 9, p. 1345-1353, Sep. 2001.
Chang, L., et al, "Effect of Sorbitol and Residual Moisture on the Stability of Lyophilized Antibodies: Implications for the Mechanism of Protein Stabilization in the Solid State", Journal of Pharmaceutical Sciences, Amer Pharmacists Association, Jul. 2005, vol. 94, No. 7, p. 1445-1455.
Sarciaux, J.M., et al., "Effects of Buffer Composition and Processing Conditions on Aggregation of Bovine IgG during Freeze-Drying", Journal of Pharmaceutical Sciences, American Pharmaceutical Association, Dec. 1999, vol. 88, p. 1354-1361, XP000865432.
Schneid, S.C., et al, "Optimization of the Secondary Drying Step in Freeze Drying Using TDLAS Technology", AAPS PharmSciTech, Mar. 2011, vol 12, No. 1, p. 379-387.
Schneid, S.C., et al, "Non-Invasive Product Temperature Determination during Primary Drying using Tunable Diode Laser Absorption Spectroscopy", Journal of Pharmaceutical Sciences, Sep. 2009, vol. 98, No. 9, p. 3406-3418.
Towns, J.K., "Moisture content in proteins: its effects and measurement", Journal of Chromatography A, vol. 705, 1995, p. 115-127, Elsevier Science Pub, XP004038941.
Ferro-Flores, G., et al, "An efficient, reproducible and fast preparation of 188Re-anti-CD20 for the treatment of non-Hodgkin's lymphoma", Nuclear Medicine Communications, 2005, vol. 26, p. 793-799.

* cited by examiner

*Primary Examiner* — Yunsoo Kim
(74) *Attorney, Agent, or Firm* — Nath, Goldberg & Meyer; Joshua B. Goldberg

(57) ABSTRACT

The present invention provides a method for preparation of a lyophilized formulation of an anti-CD 20 antibody as well as to a lyophilized formulation of an anti-CD 20 antibody, comprising an anti-CD 20 antibody and having a residual moisture content in the range of 1% to 10%. The present invention also relates to the reconstituted formulation obtained by the method described herein, the use of said antibody formulation as a medicament, the use of the lyophilized formulation for the preparation of a medicament and a method of treating a patient.

29 Claims, 5 Drawing Sheets
Specification includes a Sequence Listing.

FORMULATION OF AN ANTIBODY AND USE THEREOF

This application is a National Phase Application filed under 35 U.S.C. 371 as the US national stage of PCT/EP2014/055279, filed Mar. 17, 2014, which claims priority to EP 13159325.3, filed Mar. 15, 2013, and U.S. 61/787,225, filed Mar. 15, 2013; the content of each of which is hereby incorporated by reference in its entirety.

TECHNICAL FIELD

The present invention relates to a method for providing a lyophilized formulation of an anti-CD 20 antibody as well as to a lyophilized formulation of an anti-CD 20 antibody, comprising an anti-CD 20 antibody and having a residual moisture content in the range of 1% to 10%. Furthermore, the present invention relates to the reconstituted formulation obtained by the method described herein, the use of said antibody formulation as a medicament, the use of the lyophilized formulation for the preparation of a medicament and a method of treating a patient.

BACKGROUND

A number of criteria, e.g. as regards stability, administration and concentration are of importance in the regulatory approval proceedings of therapeutically active proteins as a drug. For example, during manufacturing, storage and delivery chemical and/or physical degradation of therapeutic proteins such as antibodies may occur, which may lead to a loss of their pharmaceutical potency and increased risk of side effects, e.g. unwanted immune response.

Further, many therapeutically active proteins need to be administered in high doses in order to achieve their desired therapeutic effect. High concentration formulations of therapeutic proteins may also be advantageous, as they may allow for a more convenient mode of administration of the therapeutic protein to the patient.

In particular, high concentrations of e.g. at least 100 mg/mL therapeutic protein may be desirable as the volume necessary for the administration of the therapeutic dose decreases with increasing concentration. Smaller volumes provide the advantage that they may be injected via less invasive routes (such as subcutaneous injection instead of intravenous infusion), which is more convenient for the patient and potentially associated with less risks for side effects like infusion reactions. A further advantage provided by high concentration formulations is that they may allow reducing the frequency of administration of the therapeutic protein to the patient.

However, the provision of high concentrated liquid formulations of therapeutically active proteins such as monoclonal antibodies is challenging as the viscosity of the liquid formulation as well as the tendency of proteins to form aggregates may increase dramatically at higher concentrations. Aggregates can contain degradation products of the protein and may lead to unwanted side effects, e.g. triggering unwanted immune responses. In order to avoid stability problems such as the formation of aggregates, protein or antibody formulations may be lyophilized.

However, lyophilized antibody formulations which are prepared by various methods exhibit differing stability upon storage. Hence, different methods and formulations for providing a stable lyophilized antibody have been described.

WO 03/009817 describes a lyophilized formulation of an IgG antibody, said formulation comprising more than 50 mg/mL of the antibody in a histidine buffer (5-25 mM) and further comprising polysorbate and sucrose.

US 2011/0236383 discloses that by using a lyoprotectant such as sucrose or trehalose a stable lyophilized protein, in particular an antibody formulation can be provided.

WO 2008/157409 describes a stable lyophilized formulation of an antibody, in particular of the anti-alpha-4 integrin antibody natalizumab, which has been prepared by lyophilizing an aqueous formulation. The aqueous formulation which is subjected to lyophilization comprises 40 mg/mL to 50 mg/mL of the immunoglobulin in a buffer as well as polysorbate and sucrose.

High concentration antibody compositions which can be reconstituted after lyophilization are disclosed in WO 2011/017070. The compositions described in said document comprises 70-250 mg/mL of the antibody, sucrose, histidine, arginine and mannitol.

WO 2010/017296 describes a freeze-drying method in which freeze-drying is carried out above the collapse temperature, i.e. the temperature at or above which the loss of intact structure or change of original structure of the lyophilized cake occurs.

However, there is still a need for stable lyophilized antibody formulations and methods for providing the same.

SUMMARY OF THE INVENTION

One aspect of the present invention relates to a method for providing a lyophilized formulation of an anti-CD 20 antibody, comprising the steps of:

I) providing a solution comprising the anti-CD 20 antibody,
II) freezing the antibody solution,
III) subjecting the antibody solution to at least one drying step at a shelf temperature of −10° C. to 30° C., in order to obtain the lyophilized formulation
wherein in the lyophilized formulation the residual moisture content obtained is in the range of 1% to 10%, optionally in the range of 1% to 5%.

In one embodiment of the method described herein, the antibody solution is subjected to one drying step.

Another embodiment of the method described herein further includes subjecting the antibody solution to a second drying step, wherein the shelf temperature used in the second drying step is lower than the shelf temperature used in the first drying step.

According to one embodiment of the method described herein, the shelf temperature used in the second drying step is at least 2° C. lower, optionally at least 3° C. lower than the shelf temperature used in the first drying step.

In a further embodiment of the method for providing a lyophilized formulation of an anti-CD 20 antibody as described herein, the shelf temperature used in the first drying step is 8° C. and/or the shelf temperature used in the second drying step is 5° C.

In one embodiment of the method described herein, the solution provided in step (I) comprises a buffering agent, optionally a buffering agent comprising histidine or phosphate.

In another embodiment of the method described herein, the solution provided in step (I) comprises a tonicity modifying agent, optionally sucrose.

In a further embodiment of the method described herein, the solution provided in step (I) comprises a surfactant, optionally a nonionic surfactant.

In one embodiment of the method described herein, the solution provided in step (I) has a pH value in the range of 5.0 to 7.0, optionally a pH value of 5.5±0.3.

In a further embodiment of the method described herein, the solution provided in step (I) comprises
a) at least 40 mg/g anti-CD 20 antibody,
b) 5-15 mM histidine,
c) 100-150 mM sucrose, and
d) 0.05-0.5 mg/g polysorbate 20; and
wherein the solution provided in step (I) has a pH value of 5.5±0.3.

In another embodiment of the method described herein, the anti-CD 20 antibody is Veltuzumab or a fragment thereof A further aspect of the present invention relates to a method for providing a liquid formulation of an anti-CD 20 antibody, comprising providing a lyophilized formulation according to the method described herein and subsequently performing a step IV) of reconstituting the lyophilized formulation.

In one embodiment of the method for providing a liquid formulation of an anti-CD 20 antibody the liquid formulation obtained in step IV) comprises
a) at least 80 mg/mL anti-CD 20 antibody,
b) 10-40 mM buffering agent, optionally a buffering agent comprising histidine,
c) 200-400 mM tonicity modifying agent, optionally sucrose,
d) 0.2-0.5 mg/mL surfactant, optionally polysorbate 20; and has a pH value of 5.5±0.3.

A further aspect of the present invention relates to a reconstituted formulation obtained by the method for providing a liquid formulation as described herein.

Another aspect of the present invention relates to a lyophilized formulation of an anti-CD 20 antibody, comprising an anti-CD 20 antibody, optionally Veltuzumab or a fragment thereof, and having a residual moisture content in the range of 1% to 10%, optionally in the range of 1% to 5%.

In one embodiment, the lyophilized formulation disclosed herein further comprises a buffering agent, optionally a buffering agent comprising histidine or phosphate.

In another embodiment, the lyophilized formulation disclosed herein further comprises a tonicity modifying agent, optionally sucrose.

In a further embodiment, the lyophilized formulation disclosed herein further comprises a surfactant, optionally a nonionic surfactant.

Another embodiment relates to the lyophilized formulation as disclosed herein, wherein the lyophilized formulation is prepared according to the method for providing a lyophilized formulation of an anti-CD 20 antibody as described herein.

A further aspect of the present invention relates to the use of the lyophilized formulation as described herein for the preparation of a medicament.

In one embodiment of the use of the lyophilized formulation for preparation of a medicament, the medicament is for parenteral administration, optionally for subcutaneous administration.

A further aspect of the present invention relates to the lyophilized or reconstituted formulation as described herein, for use as a medicament.

In one embodiment, the medicament is for parenteral administration, in particular for subcutaneous administration.

In another embodiment, the medicament is for use in the treatment of cancer or a non-malignant disease.

In a further embodiment, the medicament is for use in the treatment of a disease selected from the group consisting of Burkitt Lymphoma, Epstein-Barr Virus Infections, B-Cell Leukemia, Chronic Lymphocytic B-Cell Leukemia, Acute Lymphoblastic Leukemia, Lymphoid Leukemia, Prolymphocytic Leukemia, Hairy Cell Leukemia, Multiple Myeloma, B-Cell Lymphoma, Marginal Zone B-Cell Lymphoma, Follicular Lymphoma, Diffuse Large B-Cell Lymphoma, Immunoblastic Large-Cell Lymphoma, Mantle-Cell Lymphoma, Non-Hodgkin Lymphoma, Lymphomatoid Granulomatosis, Plasma Cell Neoplasms, Precursor Cell Lymphoblastic Leukemia-Lymphoma, Tumor Virus Infections, Waldenstrom Macroglobulinemia, Immunoproliferative Disorders, Prolymphocytic Lymphoma, Diffuse Large B-Cell Lymphoma, Immunoblastic Large-Cell Lymphoma, Mantle-Cell Lymphoma, Lymphomatoid Granulomatosis, Lymphoproliferative Disorders, Paraproteinemias, Precursor Cell Lymphoblastic Leukemia-Lymphoma, idiopathic thrombocytopenia, Thrombocytopenic Purpura, Idiopathic Thrombocytopenic Purpura, Blood Coagulation Disorders, Blood Platelet Disorders, Blood Protein Disorders, Hematologic Diseases, Hemorrhagic Disorders, Hemostatic Disorders, Lymphatic Diseases, Purpura, Thrombocytopenia, Thrombotic Microangiopathies, Haemostatic Disorders, Vascular Diseases, Rheumatoid Arthritis, Rheumatic Diseases, Connective Tissue Diseases, Pemphigus, systemic lupus erythematosum, multiple sclerosis, Herpesviridae Infections, and/or DNA Virus Infections.

In another embodiment, the medicament is for use in the treatment of autoimmune diseases such as rheumatoid arthritis, systemic lupus erythematosum and/or pemphigus, optionally systemic lupus erythematosum.

A further aspect of the present invention relates to a method of treating a patient comprising
(i) providing a lyophilized formulation of an anti-CD20 antibody according to the method described herein,
(ii) reconstituting the lyophilized formulation, and
(iii) administering the reconstituted formulation to a patient.

In one of the embodiments of the method of treating a patient described herein, the patient has cancer or a non-malignant disease, optionally an autoimmune disease.

In one of the embodiments of the method of treating a patient described herein, the autoimmune disease is rheumatoid arthritis, systemic lupus erythematosum and/or pemphigus, optionally systemic lupus erythematosum.

DETAILED DESCRIPTION OF THE INVENTION

Figure 1:
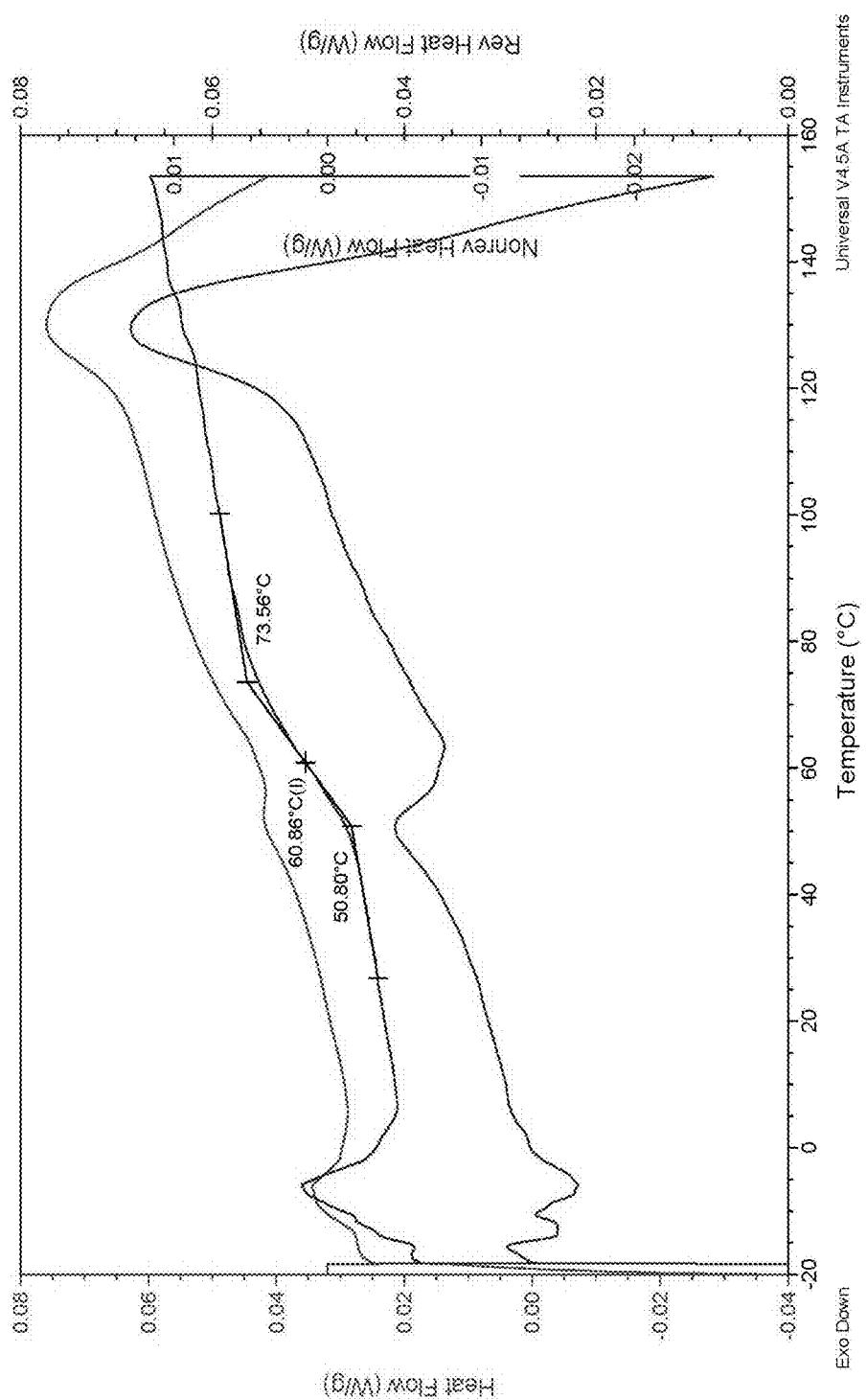
FIG. 1 depicts a DSC analysis of one sample which was prepared according to the process as described in Example 1 and wherein the secondary drying step was performed at 0° C. The upper and the lower line show the heating and the cooling curve. The cross shows the midpoint of glass transition.

Where the term "comprise" or "comprising" is used herein, it does not exclude other elements or steps. For the purpose of the present invention, the term "consisting of" is considered to be an optional embodiment of the term "comprising of". If hereinafter a group is defined to comprise at least a certain number of embodiments, this is also to be understood to disclose a group which optionally consists only of these embodiments.

Where an indefinite or a definite article is used when referring to a singular noun e.g. "a" or "an", "the", this includes a plural form of that noun unless specifically stated. Vice versa, when the plural form of a noun is used it refers also to the singular form. For example, when anti-CD 20 antibodies are mentioned, this is also to be understood as a single anti-CD 20 antibody.

Furthermore, the terms first, second, third or a), b), c) or I), II), III), (i), (ii), (iii) and the like in the description and in the claims are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein. However, in a specific embodiment of the invention, the method steps (I), (II), (III) and (IV), optionally including any intermediate steps defined herein, are performed in chronological order. In another specific embodiment, the method of treatment steps (i), (ii) and (iii), optionally including any intermediate steps defined herein, are performed in chronological order.

In the context of the present invention any numerical value indicated is typically associated with an interval of accuracy that the person skilled in the art will understand to still ensure the technical effect of the feature in question. As used herein, the deviation from the indicated numerical value is in the range of ±10%, and preferably of ±5%. The aforementioned deviation from the indicated numerical interval of ±10%, and preferably of ±5% is also indicated by the terms "about" and "approximately" used herein with respect to a numerical value.

In the context of the present invention the term "antibody" relates to full length antibodies, human antibodies, humanized antibodies, fully human antibodies, genetically engineered antibodies (e.g. monoclonal antibodies, polyclonal antibodies, chimeric antibodies, recombinant antibodies) and multispecific antibodies, as well as to fragments of such antibodies retaining the characteristic properties of the full length antibody. In one embodiment, the antibody is a humanized antibody. A "humanized antibody" is an antibody which has been modified in order to provide an increased similarity to antibodies produced in humans, e.g. by grafting a murine CDR into the framework region of a human antibody.

The term "antibody fragment" relates to a part of a full length antibody binding with the same antigen as the full length antibody. In particular, it relates to a pharmaceutically active fragment of an antibody. This part of a full length antibody may be at least the antigen binding portion or at least the variable region thereof. Genetically engineered proteins acting like an antibody are also included within the meaning of antibody fragment as used herein. Such genetically engineered antibodies may be scFv, i.e. a fusion protein of a heavy and a light chain variable region connected by a peptide linker. Further exemplary antibody fragments are Fab, Fab', F(ab')$_2$, and Fv. It is understood herein, that any reference to the antibody also includes a reference to the fragment thereof, e.g. a reference to Veltuzumab, also includes a reference to a fragment of the Veltuzumab antibody specifically binding to the CD 20 antigen.

An anti-CD 20 antibody or fragment thereof as defined herein denotes any antibody or fragment thereof that binds specifically to the CD 20 antigen (also known as CD 20, B-lymphocyte antigen CD 20, B-lymphocyte surface antigen B1, Leu-16 or Bp35). This includes anti-CD 20 antibodies having marketing approval, anti-CD 20 antibodies currently studied in clinical trials and/or any other compound which binds specifically to the CD 20 antigen. The CD 20 antigen as used herein relates to any variants, isoforms and species homologs of human CD 20. Anti-CD 20 antibodies as used herein, relates to type I anti-CD 20 antibodies as well as to type II anti-CD 20 antibodies, which differ in their mode of CD 20 binding and their biological activities. Examples of anti-CD 20 antibodies are Veltuzumab, Rituximab, Ocrelizumab, Ofatumumab, $Y^{90}$ Ibritumomab tiuxetan, $I^{131}$ tositumab, TRU-015, AME-133v, PRO131921 humanized, GA101, 1F5 IgG2a, HI47 IgG3, 2C6 IgG1, 2H7 IgG1, AT80 IgG1, 11B8 IgG1, humanized B-Ly1 antibody IgG1 and Afutuzumab (HuMab<CD 20>). Particularly, the anti-CD 20 antibody is Veltuzumab or a fragment thereof.

Veltuzumab is a monoclonal humanized anti-CD 20 antibody of the class IgG1/κ composed of mature heavy and light chains of 451 and 213 amino acid residues, respectively. Heavy and light chain amino acid sequences of Veltuzumab are set out below (SEQ ID NO: 1 and SEQ ID NO: 2, respectively):

```
Heavy Chain
                                                              (SEQ ID NO: 1)
     1     QVQLQQSGAE  VKKPGSSVKV  SCKASGYTFT  SYNMHWVKQA  PGQGLEWIGA

51     IYPGNGDTSY  NQKFKGKATL  TADESTNTAY  MELSSLRSED  TAFYYCARST

101     YYGGDWYFDV  WGQGTTVTVS  SASTKGPSVF  PLAPSSKSTS  GGTAALGCLV

151     KDYFPEPVTV  SWNSGALTSG  VHTFPAVLQS  SGLYSLSSVV  TVPSSSLGTQ

201     TYICNVNHKP  SNTKVDKRVE  PKSCDKTHTC  PPCPAPELLG  GPSVFLFPPK

251     PKDTLMISRT  PEVTCVVVDV  SHEDPEVKFN  WYVDGVEVHN  AKTKPREEQY
```

```
                                -continued
301     NSTYRVVSVL  TVLHQDWLNG  KEYKCKVSNK  ALPAPIEKTI  SKAKGQPREP

351     QVYTLPPSRE  EMTKNQVSLT  CLVKGFYPSD  IAVEWESNGQ  PENNYKTTPP

401     VLDSDGSFFL  YSKLTVDKSR  WQQGNVFSCS  VMHEALHNHY  TQKSLSLSPG

451     K

Light Chain
                                                        (SEQ ID NO: 2)
  1     DIQLTQSPSS  LSASVGDRVT  MTCRASSSVS  YIHWFQQKPG  KAPKPWIYAT

51     SNLASGVPVR  FSGSGSGTDY  TFTISSLQPE  DIATYYCQQW  TSNPPTFGGG

101     TKLEIKRTVA  APSVFIFPPS  DEQLKSGTAS  VVCLLNNFYP  REAKVQWKVD

151     NALQSGNSQE  SVTEQDSKDS  TYSLSSTLTL  SKADYEKHKV  YACEVTHQGL

201     SSPVTKSFNR  GEC
```

Anti-CD 20 antibodies according to the present invention may be monoclonal or polyclonal antibodies. Methods for production of monoclonal and polyclonal antibodies are known in the art and include e.g. the hybridoma technology and recombinant DNA methods. In one embodiment of the invention, the anti-CD 20 antibody is a monoclonal antibody.

According to the present invention, the term "IgG antibody" relates to a therapeutically useful antibody or fragment thereof falling within the IgG class (isotype) of antibodies and having a gamma-type (γ) heavy chain. This includes an antibody of any subtype of the IgG class known in the art, i.e. IgG1, IgG2, IgG3 or IgG4. In one embodiment, the antibody is a IgG1 antibody. It is understood herein that IgG antibodies also include antibodies binding specifically to the CD 20 antigen and vice versa. One exemplary IgG antibody of the present invention is Veltuzumab.

It is understood that "binds specifically" or "specifically binding" relates to an antibody having a binding affinity to the CD 20 antigen as defined herein of $\leq 10^{-9}$ mol/l, particularly of $\leq 10^{-10}$ mol/l. Methods for determining the binding affinity of antibodies to antigens are known in the art and include e.g. the use of surface plasmon resonance.

"Surfactant" as used herein relates to a surface-active agent, which is pharmaceutically acceptable. Surfactants can protect the therapeutically active protein (e.g. the antibody as defined herein) from stress such interfacial tension between two liquids or between a liquid and a solid and/or can reduce the tendency to aggregate or the formation of particulates. Pharmaceutically acceptable surfactants include non-ionic surfactants, e.g. polysorbates and poloxamers but are not limited thereto. Exemplary surfactants useful in the present invention are polyoxyethylen-polyoxypropylene copolymers (e.g. Poloxamer 188), polyoxyethylene alkyl ethers polysorbates (e.g. Polysorbate 20, Polysorbate 80) and hydroxypropyl-β-cyclodextrine. It is understood that also combinations of surfactants, e.g. combinations of the aforementioned surfactants may be used.

In the context of the present invention "pharmaceutically acceptable" relates to any compound which may be used in a pharmaceutical composition without causing any undesired effects (such as negative side effects) in a patient to which the composition is administered.

"Tonicity modifying agent" as used herein refers to any pharmaceutically acceptable agent suitable to provide an isotonic formulation. Isotonic formulations are formulations having the same tonicity (i.e. solute concentration) as the formulation to which they are compared (e.g. whole blood, blood serum or physiologic salt solution). Suitable tonicity modifying agents within the meaning of the present invention include NaCl, potassium chloride, glycine, glycerol, salts, amino acids, sugar alcohols (e.g. sorbitol and mannitol) and sugars (e.g. glucose, sucrose, trehalose, raffinose and glucose). Optionally, the tonicity modifying agent is a sugar or a sugar alcohol. In a specific embodiment, the tonicity modifying agent is a sugar such as glucose, sucrose, trehalose, raffinose and glucose, in particular sucrose. It is understood that combinations of tonicity modifying agents, in particular combinations of the aforementioned tonicity modifying agents may also be used. In particular, it is understood that the tonicity modifying agent may be used in order to provide a physiologic tonicity in the formulation, i.e. a formulation having essentially the same tonicity as human blood. Such formulations will generally have an osmolarity of approximately 300 mOsm/kg, particularly 310 mOsm/kg.

As used herein the term "histidine" specifically includes L-histidine unless otherwise specified.

"Patients" as used herein relates to any mammalian, in particular a human, suffering from any of the diseases or conditions mentioned herein, having been diagnosed with any of the diseases and/or conditions mentioned herein, being predisposed to any of the diseases and/or conditions mentioned herein or susceptible to any of the diseases and/or conditions mentioned herein.

According to the present invention "treatment" or "therapy" relates to therapeutic and/or preventive treatment of patients as defined herein.

As used herein, "stable" or "stabilized" in relation to an antibody formulation of the present invention relates to an antibody formulation retaining its chemical stability and/or physical stability during storage. Methods for determining the stability of an antibody formulation are known in the art. In particular, a stable or stabilized antibody formulation retains its chemical and/or physical stability for at least one month, at least two, at least three, at least four, at least five, at least six, at least seven, at least eight or at least nine months upon storage at room temperature. Room temperature as used herein defines a temperature in the range of 18° C. to 25° C., in particular about 19° C. to about 22° C. Specifically, room temperature denotes about 20° C. In one embodiment, a stable/stabilized antibody formulation as used herein retains its chemical and/or physical stability for at least three, at least four, at least five, at least six, at least seven, at least eight or at least nine months upon storage at 25° C. If stored at 2-8° C. the stable/stabilized antibody formulation described herein retains its chemical and/or physical stability for at least nine, at least ten, at least eleven or at least 12 months. The stable/stabilized antibody formulation disclosed herein may even retain its chemical and/or physical stability for at least one, at least two or at least three months under accelerated storage conditions, i.e. at storage at about 40° C.

"Residual moisture content" as used herein relates to the moisture content in the lyophilized cake remaining after drying has been completed. For example, the residual moisture content is determined after the single drying step or after the second drying step in the method for providing a lyophilized formulation of an anti-CD 20 antibody as described herein is completed. In particular, the term "residual moisture content" as used herein does not relate to any moisture contents present in the solution comprising an anti-CD 20 antibody before or during the method for providing a lyophilized formulation as described herein. Methods for determining the residual moisture content are known to the person skilled in the art and include thermogravimetric analysis measures and the Karl Fischer method. The latter includes two methods, i.e. the volumetric and the coulometric Karl Fischer titration. In the coulometric Karl Fischer titration a titration cell containing an anode solution, an analyte and a cathode which is submerged in the analyte is used and iodine is generated electrochemically during titration. The amount of water present is determined by the amount of electrical current used to generate iodine. This method may be used to detect water present in trace amounts in the sample. In the volumetric Karl Fischer titration iodine is added during titration. This method is mainly suitable for samples wherein water is present in larger amounts. In one embodiment, the residual moisture content is determined by means of Karl Fischer titration. Percentages given herein for the residual moisture content relate to the average water content in the lyophilized formulation.

The term "reconstitution time" as used herein relates to the time which is required in order to rehydrate a lyophilized formulation to a particle-free and clear solution, i.e. the time between adding the lyophilized formulation to a solvent and obtaining a visually clear solution.

The terms "lyophilized" and "freeze-dried" are used as synonyms within the context of the present invention. As used herein, the term "lyophilized formulation" means a lyophilisate and generally relates to a dry powder or cake-like substance, so-called lyophilized cake, obtained after lyophilization has been completed. In the context of the medical use of a lyophilized formulation as described herein, it may be applicable to reconstitute the dry powder or cake-like substance in a pharmaceutically acceptable reconstitution medium (diluent) before administration, e.g. in order to allow for parenteral administration, in particular subcutaneous or intravenous administration. The term "reconstituted formulation" as used herein in connection with the formulation according to the invention denotes a formulation which is lyophilized and re-dissolved by addition of a reconstitution medium. In the context of compounding the term pre-lyophilized formulation is used for the formulation which will be subjected to the lyophilization/freeze drying process.

"Shelf temperature" as used herein refers to the temperature in a device in which the lyophilization is performed. For example, the term "shelf temperature" refers to the temperature of the shelf in the device in which the lyophilization is performed and on which the containers containing the pre-lyophilized formulation are placed. The shelf temperature has to be distinguished from the product temperature, i.e. the temperature which the solution subjected to lyophilization actually has.

As used herein, the term "diafiltration" relates to a process using an ultrafiltration membrane in order to remove, replace, or lower the concentration of solvents from compositions comprising proteins, peptides, nucleic acids, or other biomolecules, in particular antibodies. By means of diafiltration, purification, concentration and, if necessary, buffer exchange may be performed in a single operation unit. Diafiltration devices are known in the art and include e.g. the Tangential Flow Filtration (TFF) Unit Minim II provided by Pall.

As used herein "ultrafiltration" may denote any membrane filtration process for purifying and/or concentrating macromolecular solutions, wherein hydrostatic pressure is used in order to filtrate a liquid through a semipermeable membrane with appropriate chemical and physical properties. In one embodiment, ultrafiltration is used for concentrating macromolecular solutions. Such an ultrafiltration membrane is typically characterized by the size of the molecule which is retained by the membrane, which as used herein ranges from 0.2 kDa to 200 kDa. In one embodiment, a membrane with a molecular weight cut-off of 10 kDa to 50 KDa, in particular 30 kDa is used.

As used herein "dialysis" relates to any process wherein molecules are purified by means of their different diffusion rates through a semipermeable membrane. Suitable methods for purification by means of dialysis are known to the person skilled in the art.

Further definitions of the terms will be given below in the context of which the terms are used.

As has been described above, there is a need for stable lyophilized formulations of antibodies. It has now been found that a lyophilisate having a specific residual moisture content and a composition described herein is stable and has a reduced tendency to form aggregates. It has furthermore been found that such lyophilisates may be provided with the method disclosed herein. Hence, the present invention relates to stable lyophilized formulations and methods for providing the same.

Lyophilization or freeze-drying is a process which may be used in the preparation of pharmaceutical compositions. During said process a liquid composition containing the pharmaceutically active ingredient is frozen and subsequently subjected to a vacuum to remove water in the form of ice, while leaving the remaining contents in the form of a powder or cake-like substance having a low residual moisture content. During such a lyophilization process the liquid composition containing the active ingredient is in general subjected to three main steps, i.e. freezing, primary drying and secondary drying. The lyophilization method described herein does not necessarily require a second drying step, also called desorption step, at temperatures which are elevated compared to the temperatures used in the first drying step. The process described herein provides lyophilized compositions having a specific residual moisture content which is higher than the residual moisture content of about 0.5% usually exhibited by lyophilized antibody formulations. The lyophilized compositions obtained by said process exhibit an increased stability and a reduced tendency to form aggregates, both features considered useful for antibody formulations to be administered to a patient.

The method for providing a lyophilized formulation of an anti-CD 20 antibody according to the present invention comprises the steps of:
I) providing a solution comprising the anti-CD 20 antibody,
II) freezing the antibody solution,
III) subjecting the antibody solution to at least one drying step at a shelf temperature of −10° C. to 30° C., in order to obtain the lyophilized formulation,
wherein the lyophilized formulation has a residual moisture content in the range of 1% to 10%, optionally in the range of 1% to 5%.

Step I) of the above described method relates to the provision of a "pre-lyophilized solution", i.e. the provision of a solution comprising the anti-CD 20 antibody to be subjected to lyophilization.

The solution containing the anti-CD 20 antibody may be provided by any method known to the person skilled in the art.

In one embodiment, a bulk drug substance comprising the antibody or a fragment thereof as defined herein is used as a starting material in order to provide the composition comprising the antibody. Bulk drug substances include e.g. those provided by industrial suppliers, which contain the anti-CD 20 antibody Veltuzumab. This starting material may be purified in order to remove undesired ingredients and to provide the antibody or a fragment thereof in the desired starting concentration. Purification and/or concentration adjustment may be performed by any method known in the art, such as filtration or centrifugation, respectively. Filtration includes any conventional filtration method for static filtration (e.g. vacuum filtration) and/or dynamic filtration (e.g. tangential flow filtration, diafiltration). In one embodiment of the method according to the invention, purification and/or concentration adjustment is performed by means of diafiltration (DF), ultrafiltration (UF) or dialysis.

The anti-CD 20 antibody present in the pre-lyophilized solution provided in step I) may be any anti-CD 20 antibody as defined herein. In particular, the anti-CD 20 antibody may be an anti-CD 20 antibody selected from the group consisting of Veltuzumab, Rituximab, Ocrelizumab, Ofatumumab, $Y^{90}$ Ibritumomab tiuxetan, $I^{131}$ tositumab, TRU-015, AME-133v, PRO131921 humanized, GA101, 1F5 IgG2a, H147 IgG3, 2C6 IgG1, 2H7 IgG1, AT80 IgG1, 11B8 IgG1, humanized B-Ly1 antibody IgG1 and Afutuzumab (HuMab<CD 20>). Particularly, the anti-CD 20 antibody is Veltuzumab or a fragment thereof.

The solvent used in order to provide the pre-lyophilized solution may be any solvent considered suitable by the person skilled in the art and being pharmaceutically acceptable. In one embodiment, the solution provided in step I) is an aqueous solution, i.e. a solution wherein the solvent is water. In another embodiment, the solution provided in step I) is a mixture of an aqueous solution with t-buOH. The amount of anti-CD 20 antibody present in the pre-lyophilized solution provided in step I) is determined by taking into account the desired final concentration which may depend on the dose volume and the mode of administration. Hence, the amount of the anti-CD 20 antibody in the pre-lyophilized solution may be at least 20 mg/g, at least 30 mg/g, at least 40 mg/g, at least 50 mg/g, at least 60 mg/g, at least 70 mg/g, at least 80 mg/g, at least 90 mg/g or at least 100 mg/g. In one embodiment, the amount of anti-CD 20 antibody in the pre-lyophilized formulation is at least 40 mg/g. In another embodiment, the amount of anti-CD 20 antibody in the pre-lyophilized formulation is 50 mg/g. Suitable amounts of anti-CD 20 antibody may also lie within the range of 20-100 mg/g, 30-70 mg/g or 40-60 mg/g.

The pre-lyophilized formulation provided in step I) may be a pH-buffered solution, i.e. a solution comprising a buffering agent. As used herein a buffering agent denotes a weak acid or base allowing to maintain the pH-value in a solution at a nearly constant level, such as phosphate, acetate (e.g., sodium acetate), succinate (e.g. sodium succinate), gluconate, glutamate, citrate, Tris, other organic acid buffering agents and amino acids such as alanine, arginine, asparagine, aspartic acid, cysteine, glutamic acid, glutamin, glycine, histidine, isoleucine, leucine, lysine, methionine, phenylalanine, proline, serine, threonine, tryptophan, tyrosine, valine, specifically histidine. Buffering agents comprising amino acids are known to the person skilled in the art and can be chosen according to their desired buffering properties. Exemplary histidine buffering agents are histidine, histidine hydrochloride, histidine hydrochloride monohydrate, histidine acetate, histidine phosphate, histidine sulfate and mixtures thereof. It is understood, that any of the herein mentioned buffering agents may be used either alone or in combination with another buffering agent considered suitable by the person skilled in the art. In one embodiment, the buffering agent present in the pre-lyophilized formulation is histidine or phosphate. In another embodiment, the buffering agent is histidine and/or histidine hydrochloride monohydrate.

The buffering agent as defined herein may be present in a concentration in the range of 5 to 50 mM, optionally in the range of 5-15 mM or 20-40 mM. In some embodiments, the buffering agent, which is optionally histidine or phosphate, is present in a concentration of 5 mM, 10 mM, 15 mM, 20 mM, 25 mM, 27 mM, 30 mM, 35 mM, 40 mM, 45 mM or 50 mM. In one embodiment, the buffering agent, optionally histidine or phosphate, is present in a concentration of 10 mM in the pre-lyophilized solution provided in step I).

The pH of the pre-lyophilized solution provided in step I) may be in the range of 4.0 to 8.0, optionally in the range of 5.0 to 7.0, in particular in the range of 5.0 to 6.0. In some embodiments, the pre-lyophilized solution has a pH-value of 5.5±0.3, 5.5±0.2 or 5.5±0.1.

The pre-lyophilized solution provided in step I) may further comprise a tonicity modifying agent as defined herein. It is understood by the person skilled in the art that the pre-lyophilized solution may not only comprise one tonicity modifying agent as defined herein, but also combinations of two or more tonicity modifying agents, e.g. a combination of sucrose and raffinose. In one embodiment, the tonicity modifying agent is a sugar or a sugar alcohol. In a specific embodiment, the tonicity modifying agent is a sugar selected from the group consisting of sucrose, trehalose and glucose, in particular sucrose. In another embodiment, the tonicity modifying agent is a sugar alcohol selected from sorbitol and mannitol, in particular mannitol.

The tonicity modifying agent may be present in a concentration in the range of 100 to 200 mM, in particular in the range of 100 to 150 mM. In one embodiment of the invention, the tonicity modifying agent is present in a concentration of 100 mM, 120 mM, 140 mM, 160 mM, 180 mM or 200 mM, in particular in a concentration of 120 mM.

It may be useful to have a specific weight ratio of anti-CD 20 antibody and tonicity modifying agent in the pre-lyophilized solution. Such a weight ratio may be selected individually for each anti-CD 20 antibody and tonicity modifying agent combination. In the case of the combination of an anti-CD 20 antibody and a sugar (such as sucrose, trehalose and glucose) as the tonicity modifying agent, the weight ratio may be from 1 to 2 parts anti-CD 20 antibody to 1 to 2 parts tonicity modifying agent. In one embodiment, the weight ratio of anti-CD 20 antibody, optionally Veltuzumab, to sugar, optionally sucrose, acting as tonicity modifying agent is 1.5 to 1.

In certain embodiments the solution provided in step I) may further comprise a surfactant as defined herein such as polyoxyethylen-polyoxypropylene copolymers (e.g. Poloxamer 188), polyoxyethylene alkyl ethers polysorbates (e.g. Polysorbate 20, Polysorbate 80) and hydroxypropyl-β-cyclodextrine. In particular, the surfactant may be selected from the group consisting of polysorbate 20, polysorbate 80 and hydroxypropyl-β-cyclodextrine. In one embodiment the surfactant present in the pre-lyophilized solution is a non-ionic surfactant, e.g. polysorbate 20 or polysorbate 80, optionally polysorbate 20.

The amount of surfactant added to the pre-lyophilized solution may be any amount considered suitable by the person skilled in the art, e.g. an amount suitable to minimize surface induced degradation of the anti-CD 20 antibody by protecting it from or reducing the influence of one or more of the following stresses: stir stress, freeze-thaw stress and/or temperature stress. For example, the amount of surfactant used may be in the range of 0.01 mg/g to 2.5 mg/g. In certain embodiments the amount of surfactant present in the pre-lyophilized formulation is 0.05 mg/g to 1 mg/g, in particular 0.05 mg/g to 0.5 mg/g. In certain embodiments the amount of surfactant, optionally polysorbate 20 or polysorbate 80 in the pre-lyophilized solution, may be about 0.01, 0.05, 0.1, 0.2, 0.3, 0.4 or 0.5 mg/g, particularly 0.1 mg/g.

In one embodiment the solution provided in step I) comprises
a) at least 40 mg/g anti-CD 20 antibody,
b) 5-15 mM buffering agent,
c) 100-200 mM tonicity modifying agent
d) 0.05-0.5 mg/g surfactant; and
has a pH value of 5.5±0.3.

In another embodiment the solution provided in step a) comprises
a) at least 40 mg/g anti-CD 20 antibody,
b) 5-15 mM buffering agent comprising histidine, optionally histidine and/or histidine hydrochloride, particularly a combination of histidine and histidine hydrochloride
c) 100-200 mM tonicity modifying agent
d) 0.05-0.5 mg/g surfactant; and
has a pH value of 5.5±0.3.

In another embodiment the solution provided in step I) comprises
a) at least 40 mg/g anti-CD 20 antibody,
b) 5-15 mM buffering agent comprising histidine, optionally of histidine and/or histidine hydrochloride, particularly a combination of histidine and histidine hydrochloride
c) 100-200 mM of a sugar as described herein as tonicity modifying agent, optionally sucrose
d) 0.05-0.5 mg/g surfactant; and
has a pH value of 5.5±0.3.

In another embodiment the solution provided in step I) comprises
a) at least 40 mg/g anti-CD 20 antibody,
b) 5-15 mM buffering agent comprising histidine, optionally of histidine and/or histidine hydrochloride, particularly a combination of histidine and histidine hydrochloride
c) 100-200 mM of a sugar as described herein as tonicity modifying agent, optionally sucrose
d) 0.05-0.5 mg/g non-ionic surfactant, optionally polysorbate 20 and/or polysorbate 80, particularly polysorbate 20; and
has a pH value of 5.5±0.3.

In a further embodiment the solution provided in step I) comprises
a) at least 40 mg/g anti-CD 20 antibody, optionally Veltuzumab
b) 5-15 mM histidine,
c) 100-200 mM sucrose
d) 0.05-0.5 mg/g polysorbate 20; and
has a pH value of 5.5±0.3.

In an alternative embodiment the solution provided in step I) comprises
a) at least 40 mg/g anti-CD 20 antibody, optionally Veltuzumab
b) 5-15 mM of a combination of histidine and histidine hydrochloride,
c) 100-200 mM sucrose
d) 0.05-0.5 mg/g polysorbate 20; and
has a pH value of 5.5±0.3.

The pre-lyophilized solution provided in step I) may further comprise any additional ingredient considered suitable by the person skilled in the art. Examplary additional ingredients are lyoprotectants and bulking agents.

"Lyoprotectants" as used herein refers to any molecule which is able to prevent or reduce chemical and/or physical instabilities of the anti-CD 20 antibody when subjected to lyophilization. Such lyoprotectants may include sugars, amino acids, methylamines, polyols and combinations thereof. However, in one embodiment, no additional lyoprotectant is added to the pre-lyophilized solution.

"Bulking agents" as used herein denotes any agent which influences the physical structure of the dry powder or cake-like substance obtained after lyophilization. Exemplary bulking agents are glycine, polyethylene glycol and mannitol. However, in one embodiment, no additional bulking agent is added to the pre-lyophilized solution.

The method described herein further includes a step II) of freezing the antibody solution provided in step I). Typically, this freezing step is performed at a temperature below the freezing temperature of the solution. In one embodiment, the freezing step is carried out at a shelf temperature in the range of −30° C. to −60° C., optionally from −30° C. to −45° C. In one embodiment, the shelf temperature used in the freezing step is about −40° C. The shelf temperature is applied for a time sufficient to allow the transformation of the liquid to the solid state. The time span needed may be dependent from the volume subjected to lyophilization, the formulation used and the type of container holding it. In the method described herein, the length of the freezing step may be at least 1 hour, at least 2 hours or at least 3 hours. Typically, the solution obtained in step I) may be subjected to the above described temperature for 45 to 180 minutes, in particular for 90 to 180 minutes. In one embodiment, the solution obtained in step I) is subjected to the above described temperature for approximately 170 minutes. The time span mentioned herein for freezing includes ramp phases in which the temperature is brought to the desired temperature at a certain rate, optionally a ramp phase to freeze prior to the actual freezing and a ramp phase after the actual freezing for evacuation. Typically, the ramp rate used in step II) is about 1° C./min.

As already described above, it has been found that in order to obtain lyophilized antibody formulations wherein the dry powder or cake-like substance obtained after completion of the lyophilization process has a residual moisture content as defined herein may be provided by the method as described herein. This method may also allow for the provision of stable residual moisture content throughout the lot. In particular, the method described herein does not necessarily require a secondary drying step at an elevated temperature. Elevated temperature as used herein with regard to the second drying step denotes any temperature which is higher than the temperature used in the first drying step. In particular, the method described herein comprises a further step III) of subjecting the antibody solution to at least one drying step at a shelf temperature of −10° C. to 30° C.

The conditions set out below relate to the method as described herein, wherein the antibody solution is subjected to only one drying step. If the antibody solution is subjected to more than one drying step, the conditions given below relate to the first (i.e. primary) drying step. Conditions for any further drying step will be provided separately.

As mentioned above, the shelf temperature used in the primary drying step is between −10° C. and 30° C. In one embodiment, the shelf temperature is in the range of −10° C. to 20° C., in particular in the range of −5° C. to 10° C. In some embodiments, the shelf temperature used in the primary drying step will be about 5° C., 6° C., 7° C., 8° C., 9° C. or 10° C., e.g. about 8° C.

In order to allow for sublimization of the frozen or unbound water a suitable pressure has to be chosen, which typically is in the range from about 0.06 mbar to about 0.3 mbar. Suitable pressure used in the primary drying step and any further drying step may be in the range from 0.1 to 0.3 mbar. In one embodiment of the method described herein, the pressure used in the primary drying step and/or any further drying step is about 0.19 mbar.

The time span for which the antibody solution is subjected to the primary drying step and/or any further drying step may be dependent from the volume subjected to lyophilization, the formulation used and/or the type of container holding it. The time required for drying can thus range from several hours to several days. Typically, the time span for which the antibody formulation is subjected to primary drying is in the range of 30 to 60 hours, optionally in the range of 30 to 45 hours. In one embodiment of the method described herein, the antibody formulation is subjected to primary drying for about 37 hours. The time span mentioned herein includes ramp phases in which the temperature is brought to the desired temperature at a certain rate, optionally a ramp phase to primary drying prior to the actual drying step. Typically, the ramp rate used in step III) for primary drying is about 1° C./min. Such a ramp phase to the primary drying step will typically have a duration of several minutes, optionally about 50 minutes. The duration of such a ramp phase may depend on the ramp rate used and the differences in the temperatures used in the freezing and drying step.

In one embodiment of the method described herein, the antibody solution is subjected to a second drying step, whereby the shelf temperature used in said second drying step is at least 2° C. to 10° C. lower, optionally at least 3° C. to 7° C. lower than the shelf temperature used in the first drying step. In one embodiment, the shelf temperature used in the second drying step is at least 2° C. lower, optionally at least 3° C. lower than the shelf temperature used in the first drying step.

In one embodiment of the method described herein, the shelf temperature used in the first drying step is −5° C. to 10° C. and the shelf temperature used in the second drying step is −8° C. to 7° C., provided the shelf temperature used in the second drying step is lower than the shelf temperature used in the first drying step. In particular, the shelf temperature in the second drying step is at least 3° C. lower than the shelf temperature used in the first drying step. In a specific embodiment of the method disclosed herein, the shelf temperature used in the first drying step is 8° C. and/or the shelf temperature used in the second drying step is 5° C.

The time span for which the antibody solution is subjected to the second drying step may be dependent from the volume subjected to lyophilization, the formulation used and/or the type of container holding it. The time required for second drying can thus range from several minutes to several hours. Typically, the time span for which the antibody formulation is subjected to second drying step is in the range of 10 to 20 hours, optionally of 3 to 7 hours. In one embodiment of the method described herein the antibody formulation is subjected to primary drying for about 5 hours. The time span mentioned herein for the second drying step includes one or more ramp phase/s in which the temperature is brought to the desired temperature at a certain rate, optionally a ramp phase to second drying prior to the actual second drying step. Typically, the ramp rate used in step III) prior to second drying is about 1° C./min. Such a ramp phase will typically have a duration of several minutes, optionally about three minutes. The duration of such a ramp phase may depend on the ramp rate used and the differences in the temperatures used in the two drying steps. The ramp phase may furthermore include a step of venting and/or stoppering the container holding the lyophilized antibody formulation. This venting and/or stoppering may take several minutes, in particular about 15 minutes.

In order to allow for sublimization of the frozen or unbound water a suitable pressure has to be chosen for the second drying step, which typically ranges from about 0.06 mbar to about 0.3 mbar. A suitable pressure used in the second drying step may be in the range from 0.1 to 0.3 mbar. In one embodiment of the method described herein, the pressure used in the second drying step is about 0.19 mbar. The pressure used in the second drying step may be the same as employed during the first drying step.

The method described herein may include additional steps, e.g. steps after the second drying step which are necessary for providing a final product, e.g. a product ready for sale. Such steps may include stoppering of the containers used for lyophilization and/or packaging of the lyophilizate obtained.

The dry powder or cake-like substance (i.e. the lyophilizate) obtained by the above described method has a residual moisture content in the range of 1% to 10%. In one embodiment the residual moisture content of the lyophilizate is in the range of 1% to 5%, optionally in the range of 1.5% to 3%, specifically 1.5% to 2.5%. As already mentioned above, lyophilizates exhibiting this specific residual moisture content which is higher than the residual moisture content used for known lyophilized antibody formulations (which is e.g. below 1%, in particular below 0.5%) are stable and show a reduced tendency to form aggregates. The method described above allows for the provision of such lyophilizates which exhibit the desired moisture content throughout the whole lot.

The dry powder or cake-like substance obtained by the above described method may be reconstituted at a desired time point, such as prior to administration to the patient. Hence, the present invention also relates to a method for providing a liquid formulation of an anti-CD 20 antibody as defined herein, wherein in a first step a lyophilized formulation is provided by steps I)-III) of the method as described herein above and in a subsequent step IV) the lyophilized formulation is reconstituted. The time needed for reconstitution is usually short, e.g. 20 minutes or less, 10 minutes or less, or 5 minutes or less. It is understood that the composition of the reconstituted formulation will depend on the composition of the lyophilized formulation used as starting product. It may be that during reconstitution and/or after reconstitution further substances are added to the solution, e.g. substances as mentioned herein, e.g. tonicity modifiers, buffering substances, and/or further antibodies.

The diluent or reconstitution medium used for reconstitution can be any pharmaceutically acceptable diluent considered suitable by the person skilled in the art. Exemplary diluents which may be used in the context of the present invention are sterile water, bacteriostatic water for injection, pH-buffered solutions such as a phosphate-buffered saline, sterile saline solutions, Ringer's solutions, dextrose solutions, sodium chloride solutions (e.g. 0.9% (w/v) NaCl), glucose solutions (e.g. 5% glucose), surfactant containing solutions (e.g. 0.01% polysorbate 20) and combinations thereof. It is understood that the diluents may include any further ingredient considered suitable and/or necessary by the person skilled in the art such as preservatives, buffering agents, tonicity modifying agents and/or further active ingredients.

Buffering agents and tonicity modifying agents which may be present in the diluents explicitly include any of the buffering agents and tonicity modifying agents mentioned herein, specifically in any of the herein described concentrations. Preservatives present in the diluents includes any compound which essentially reduces and/or prevents microbial, in particular bacterial growth and/or otherwise increases the storage time of the composition obtained after reconstitution. Exemplary preservatives include antibiotics, antimycotics and antiviral compounds.

Further active ingredients present in the diluents include any active ingredient considered suitable by the person skilled in the art, e.g. the active ingredients mentioned herein.

The volume of the diluent used will depend on the intended mode of administration and will be larger for e.g. intravenous administration than for subcutaneous administration of the anti-CD 20 antibody formulation. Furthermore, the volume of the diluents used will depend on the desired final concentration of the anti-CD 20 antibody in the formulation to be administered. When e.g. subcutaneous administration of the antibody formulation is desired, the volume of the diluent is usually limited to a volume of approximately 2 ml or less than 2 ml. This is due to viscoelastic tissue resistance and backpressure generated upon injection as well as pain perceived by the patient. Hence, as only a rather small volume of the antibody formulation can be provided with a single subcutaneous injection, it can be advantageous to have a formulation comprising a high concentration of the anti-CD 20 antibody such as a Veltuzumab antibody. This may allow administering high doses of antibodies in a small liquid volume suitable for subcutaneous injection.

Thus, in one embodiment the liquid formulation obtained in step IV), i.e. the reconstituted formulation comprises at least 80 mg/mL of the anti-CD 20 antibody. In another embodiment, the liquid formulation obtained in step IV) comprises at least 90 mg/mL, at least 100 mg/mL, at least 110 mg/mL, at least 120 mg/mL, at least 130 mg/mL, at least 140 mg/mL, at least 150 mg/mL or at least 160 mg/mL of the anti-CD 20 antibody, optionally at least 160 mg/mL of the anti-CD 20 antibody. In a further embodiment of the method described herein, the liquid formulation obtained in step IV) comprises about 110 mg/mL, about 120 mg/mL, about 130 mg/mL, about 140 mg/mL, about 150 mg/mL or about 160 mg/mL of the anti-CD 20 antibody.

In a specific embodiment, the liquid formulation obtained in step IV) of the method described herein is a formulation of an anti-CD 20 antibody selected from the group consisting of Veltuzumab, Rituximab, Ocrelizumab, Ofatumumab, $Y^{90}$ Ibritumomab tiuxetan, $I^{131}$ tositumab, TRU-015, AME-133v, PRO131921 humanized, GA101, 1F5 IgG2a, HI47 IgG3, 2C6 IgG1, 2H7 IgG1, AT80 IgG1, 11B8 IgG1, humanized B-Ly1 antibody IgG1 and Afutuzumab (HuMab<CD 20>). Particularly, the liquid anti-CD 20 antibody formulation is a formulation of Veltuzumab or a fragment thereof. During reconstitution and/or after reconstitution anti-CD 20 antibodies can be added to the solution, e.g. any of the antibodies mentioned herein, either alone or in a mixture. The antibodies may be added in solution or in dry powder or cake-like condition.

The reconstituted formulation may further contain a buffer as defined herein such as phosphate, acetate (e.g., sodium acetate), succinate (such as sodium succinate), gluconate, glutamate, citrate, Tris, other organic acid buffering agents and amino acids such as alanine, arginine, asparagine, aspartic acid, cysteine, glutamic acid, glutamin, glycine, histidine, isoleucine, leucine, lysine, methionine, phenylalanine, proline, serine, threonine, tryptophan, tyrosine, valine, specifically histidine. Buffering agents comprising amino acids are known to the person skilled in the art and can be chosen according to their desired buffering properties. Exemplary histidine buffering agents are histidine, histidine hydrochloride, histidine hydrochloride monohydrate, histidine acetate, histidine phosphate, histidine sulfate and mixtures thereof. It is understood, that any of the herein mentioned buffering agents may be used either alone or in combination with another buffering agent considered suitable by the person skilled in the art. In one embodiment, the buffering agent present in the reconstituted formulation is a buffering agent comprising histidine or phosphate. In another embodiment, the buffering agent is histidine and/or histidine hydrochloride monohydrate.

The buffering agent as defined herein may be present in the reconstituted formulation in a concentration in the range of 10 to 40 mM, optionally in the range of 20-30 mM. In some embodiments the buffering agent which is optionally histidine or phosphate, is present in a concentration of about 15 mM, about 20 mM, about 25 mM, about 30 mM, about 35 mM or about 40 mM. In one embodiment, the buffering agent, optionally histidine or phosphate, is present in a concentration of about 30 mM in the reconstituted formulation provided in step IV). In another embodiment, the buffering agent, optionally histidine or phosphate is present in a concentration of 27 mM in the reconstituted formulation.

The pH of the reconstituted formulation provided in step IV) may be in the range of 4.0 to 8.0, optionally in the range of 5.0 to 7.0, in particular in the range of 5.0 to 6.0. In some embodiments, the reconstituted solution has a pH-value of 5.5±0.3, 5.5±0.2 or 5.5±0.1, optionally 5.5±0.1.

The reconstituted formulation may further comprise a tonicity modifying agent as defined herein. It is understood by the person skilled in the art that the reconstituted formulation may not only comprise one tonicity modifying agent as defined herein, but also combinations of two or more tonicity modifying agents, e.g. a combination of sucrose and raffinose. In one embodiment, the tonicity modifying agent is a sugar or a sugar alcohol. In a specific embodiment, the tonicity modifying agent is a sugar selected from the group consisting of sucrose, trehalose and glucose, in particular sucrose. In another embodiment, the tonicity modifying agent is a sugar alcohol selected from sorbitol and mannitol, in particular mannitol.

The tonicity modifying agent may be present in the reconstituted formulation in a concentration in the range of 200 to 400 mM, in particular in the range of 300 to 350 mM. In one embodiment of the invention, the tonicity modifying agent is present in a concentration of about 300 mM, about 320 mM, about 340 mM, or about 350 mM, in particular about 320 mM.

It may be useful to have a specific weight ratio of anti-CD 20 antibody and tonicity modifying agent in the reconstituted formulation. Such a weight ratio may be selected individually for each anti-CD 20 antibody and tonicity modifying agent combination. In the case of the combination of an anti-CD 20 antibody and a sugar (such as sucrose, trehalose and glucose) as the tonicity modifying agent, the weight ratio may be from 1 to 2 parts anti-CD 20 antibody to 1 to 2 parts tonicity modifying agent. In one embodiment, the weight ratio of anti-CD 20 antibody, optionally Veltuzumab to sugar, optionally sucrose, acting as tonicity modifying agent is 1.5 to 1.

In certain embodiments the solution provided in step IV) may further comprise a surfactant as defined herein such as polyoxyethylen-polyoxypropylene copolymers (e.g. Poloxamer 188), polyoxyethylene alkyl ethers polysorbates (e.g. Polysorbate 20, Polysorbate 80) and hydroxypropyl-β-cyclodextrine. In particular, the surfactant may be selected from the group consisting of polysorbate 20, polysorbate 80 and hydroxypropyl-β-cyclodextrine. In one embodiment, the surfactant present in the pre-lyophilized solution is a non-ionic surfactant e.g. polysorbate 20 or polysorbate 80, optionally polysorbate 20.

The amount of surfactant in the reconstituted formulation may be any amount considered suitable by the person skilled in the art, e.g. an amount suitable to minimize surface induced degradation of the anti-CD 20 antibody by protecting it from or reducing the influence of one or more of the following stresses: stir stress, freeze-thaw stress and/or temperature stress. For example, the amount of surfactant used may be in the range of 0.2 mg/mL to 0.5 mg/mL. In certain embodiments, the amount of surfactant optionally polysorbate 20 or polysorbate 80 in the pre-lyophilized solution, may be about 0.2, 0.25, 0.3, 0.4 or 0.5 mg/mL, in particular about 0.3 mg/mL.

One embodiment relates to the method described herein, wherein the liquid formulation obtained in step IV) comprises a) at least 80 mg/mL anti-CD 20 antibody,
b) 10-40 mM buffering agent,
c) 200-400 mM tonicity modifying agent,
d) 0.2-0.5 mg/mL surfactant; and
has a pH value of 5.5±0.3.

Another embodiment relates to the method described herein, wherein the liquid formulation obtained in step IV) comprises a) at least 80 mg/mL anti-CD 20 antibody,
b) 10-40 mM buffering agent comprising histidine, optionally histidine and/or histidine hydrochloride, particularly a combination of histidine and histidine hydrochloride,
c) 200-400 mM tonicity modifying agent,
d) 0.2-0.5 mg/mL surfactant; and
has a pH value of 5.5±0.3.

Another embodiment relates to the method described herein, wherein the liquid formulation obtained in step IV) comprises a) at least 80 mg/mL anti-CD 20 antibody,
b) 10-40 mM buffering agent comprising histidine, optionally histidine and/or histidine hydrochloride, particularly a combination of histidine and histidine hydrochloride,
c) 200-400 mM of a sugar as described herein as tonicity modifying agent, optionally sucrose,
d) 0.2-0.5 mg/mL surfactant; and
has a pH value of 5.5±0.3.

Another embodiment relates to the method described herein, wherein the liquid formulation obtained in step IV) comprises a) at least 80 mg/mL anti-CD 20 antibody,
b) 10-40 mM buffering agent comprising histidine, optionally histidine and/or histidine hydrochloride, particularly a combination of histidine and histidine hydrochloride,
c) 200-400 mM of a sugar as described herein as tonicity modifying agent, optionally sucrose,
d) 0.2-0.5 mg/mL non-ionic surfactant, optionally polysorbate 20 and/or polysorbate 80, particularly polysorbate 20; and
has a pH value of 5.5±0.3.

Another embodiment relates to the method described herein, wherein the liquid formulation obtained in step IV) comprises a) at least 80 mg/mL anti-CD 20 antibody, optionally Veltuzumab
b) 10-40 mM histidine,
c) 200-400 mM sucrose,
d) 0.2-0.5 mg/mL polysorbate 20; and
has a pH value of 5.5±0.3.

An alternative embodiment relates to the method described herein, wherein the liquid formulation obtained in step IV) comprises a) at least 80 mg/mL anti-CD 20 antibody, optionally Veltuzumab
b) 10-40 mM of a combination of histidine and histidine hydrochloride,
c) 200-400 mM sucrose,
d) 0.2-0.5 mg/mL polysorbate 20; and
has a pH value of 5.5±0.3.

The liquid formulation obtained in step IV) may additionally comprise a lyoprotectant and/or a bulking agent. However, in one embodiment the liquid formulation does not comprise an additional lyoprotectant and/or bulking agent.

In one embodiment, the reconstituted formulation has an osmolarity of ≥240 mOsm/kg. In certain embodiments, the reconstituted formulation has an osmolarity in the range of 240 mOsm/kg to 700 mOsm/kg.

In another of its aspects, the present invention also relates to the reconstituted formulation obtained by the method described herein. It is understood, that the reconstituted formulation obtained by the method described herein, may be any reconstituted formulation described with respect to the reconstituted formulation obtained in step IV) of the method described herein.

As already described above, it has been found that lyophilized formulations having a specific residual moisture content which is higher than the moisture content generally used in antibody lyophilizates have a reduced tendency to form aggregates and increased stability upon storage.

Hence, the present invention also relates to a lyophilized formulation of an anti-CD 20 antibody, comprising an anti-CD 20 antibody, optionally Veltuzumab, and having a residual moisture content in the range of 1% to 10%. In one embodiment, the residual moisture content of the lyophilized formulation is in the range of 1% to 5%, optionally in the range of 1.5% to 3%, specifically 1.5% to 2.5%.

It is understood, that the composition of the lyophilized formulation may depend on the composition of the pre-lyophilized solution from which it is derived. In particular, the amount of each compound present in the lyophilized formulation will be dependent from the amount present of the respective compound in the pre-lyophilized formulation from which it is derived.

The anti-CD 20 antibody present in the lyophilized formulation may be any anti-CD 20 antibody as defined herein. In particular, the anti-CD 20 antibody may be an anti-CD 20 antibody selected from the group consisting of Veltuzumab, Rituximab, Ocrelizumab, Ofatumumab, $Y^{90}$ Ibritumomab tiuxetan, $I^{131}$ tositumab, TRU-015, AME-133v, PRO131921 humanized, GA101, 1F5 IgG2a, HI47 IgG3, 2C6 IgG1, 2H7 IgG1, AT80 IgG1, 11B8 IgG1, humanized B-Ly1 antibody IgG1 and Afutuzumab (HuMab<CD 20>). Particularly, the anti-CD 20 antibody is Veltuzumab or a fragment thereof.

The amount of anti-CD 20 antibody present in the lyophilized formulation depends on the amount of anti-CD 20 antibody present in the pre-lyophilization fluid, which, in turn, is set by taking into account the desired final concentration. The desired final concentration may depend on the dose volume and the mode of administration. Hence, the amount of the anti-CD 20 antibody in the lyophilized formulation may be at least 40 wt %, at least 50 wt %, at least 60 wt % or at least 70 wt % of the lyophilized formulation, in particular about 50 wt % of the lyophilized formulation.

In a further embodiment, the lyophilized formulation further comprises a buffering agent. As used herein, a buffering agent denotes a weak acid or base allowing to maintain the pH-value in a solution at a nearly constant level, such as phosphate, acetate (e.g., sodium acetate), succinate (such as sodium succinate), gluconate, glutamate, citrate, Tris, other organic acid buffering agents and amino acids e. g. alanine, arginine, asparagine, aspartic acid, cysteine, glutamic acid, glutamin, glycine, histidine, isoleucine, leucine, lysine, methionine, phenylalanine, proline, serine, threonine, tryptophan, tyrosine, valine, specifically histidine. Buffering agents comprising amino acids are known to the person skilled in the art and can be chosen according to their desired buffering properties. Exemplary histidine buffering agents are histidine, histidine hydrochloride, histidine hydrochloride monohydrate, histidine acetate, histidine phosphate, histidine sulfate and mixtures thereof. It is understood, that any of the herein mentioned buffering agents may be used either alone or in combination with another buffering agent considered suitable by the person skilled in the art. In one embodiment, the buffering agent present in the lyophilized formulation is histidine or phosphate. In another embodiment, the buffering agent is histidine and/or histidine hydrochloride monohydrate. It is understood, that the amount of buffering agent present in the lyophilized formulation will depend on the the amount of buffering agent present in the pre-lyophilized formulation from which it is derived.

The buffering agent as defined herein for the lyophilized formulation may be present in an amount correlating to the concentration of buffering agent present in the pre-lyophilized formulation. Hence, in one embodiment, about 2 wt % buffering agent, in particular histidine and histidine hydrochloride, are present in the lyophilized formulation.

Another embodiment relates to a lyophilized formulation further comprising a tonicity modifying agent as defined herein. The amount of tonicity modifying agent present in the lyophilized formulation depends on the amount of tonicity modifying agent present in the formulation subjected to lyophilization. It is understood by the person skilled in the art that the lyophilized formulation may not only comprise one tonicity modifying agent as defined herein, but also combinations of two or more tonicity modifying agents, e.g. a combination of sucrose and raffinose. In one embodiment, the tonicity modifying agent is a sugar or a sugar alcohol. In a specific embodiment, the tonicity modifying agent is a sugar selected from the group consisting of sucrose, trehalose and glucose, in particular sucrose. In another embodiment, the tonicity modifying agent is a sugar alcohol selected from sorbitol and mannitol, in particular mannitol.

The tonicity modifying agent may be present in an amount correlating to the concentration present in the pre-lyophilized formulation, which is in the range defined above.

In certain embodiments the lyophilized formulation may further comprise a surfactant as defined herein such as polyoxyethylen-polyoxypropylene copolymers (e.g. Poloxamer 188), polyoxyethylene alkyl ethers polysorbates (e.g. Polysorbate 20, Polysorbate 80) and hydroxypropyl-β-cyclodextrine. Again, if, which and the amount of surfactants are present in the lyophilized formulation depends from the composition of the formulation which was subjected to lyophilization. In particular, the surfactant may be selected from the group consisting of polysorbate 20, polysorbate 80 and hydroxypropyl-β-cyclodextrine. In one embodiment, the surfactant present in the pre-lyophilized solution is a non-ionic surfactant e.g. polysorbate 20 or polysorbate 80, optionally polysorbate 20.

The amount of surfactant in the lyophilized formulation may be any amount considered suitable by the person skilled in the art, e.g. an amount suitable to minimize surface induced degradation of the anti-CD 20 antibody by protecting it from or reducing the influence of one or more of the following stresses: stir stress, freeze-thaw stress and/or temperature stress and depends on the amount of surfactant present in the formulation subjected to lyophilization. For example, the amount of surfactant used may be in the range of 0.1 mg/g to 2.0 mg/g. In certain embodiments, the amount of surfactant present in the pre-lyophilized formulation is 1.0 mg/g to 2.0 mg/g, in particular about 1.0 mg/g.

In one embodiment the lyophilized formulation described herein is prepared according to the method for providing a lyophilized formulation of an anti-CD 20 antibody described herein.

One aspect of the present invention relates to the use of the lyophilized formulation as described herein for the preparation of a medicament.

When used for the preparation of a medicament, the lyophilized formulation as described herein may be reconstituted with a reconstitution medium as described herein, in order to allow for an administration to a patient. Said patient may be suffering from one or more of the diseases and/or conditions as described herein. In one embodiment, the patient is suffering from a non-malignant disease and/or an autoimmune disease, e.g. rheumatoid arthritis, systemic lupus erythematosum, thrombocytopenia purpura and/or pemphigus. In particular, the patient is suffering from systemic lupus erythematosum.

It is understood, that in one embodiment the lyophilized formulation used for the preparation of a medicament may be obtained by the method for providing a lyophilized formulation of an anti-CD 20 antibody as described herein.

In another embodiment, the lyophilized formulation may be used for the preparation of a medicament for parenteral administration, e.g. for subcutaneous, intravenous, intradermal, intramuscular, intramammary, intraperitoneal, intrathecal, retrobulbar, intrapulmonary administration and/or surgical implantation at a particular site. In particular, the lyophilized formulation described herein and/or obtained by the method described herein is used for the preparation of a medicament for subcutaneous administration.

Another aspect of the invention relates to the lyophilized formulation as described herein for use as a medicament.

As already noted above, it is understood herein, that when used in the context of its medical use, the term "lyophilized formulation" also includes the reconstituted formulation obtained by dissolving the lyophilizate in a diluent as disclosed herein, which may subsequently be administered e.g. via intravenous or subcutaneous injection to a patient. Hence, any features provided above for the reconstituted formulation are also applicable for the lyophilized formulation when used as a medicament.

The medicament will be administered to a patient in need of the treatment with anti-CD 20 antibodies via any administration route considered suitable by the person skilled in the art. For example, it may be administered to a patient subcutaneously or via other parenteral routes. Other parenteral routes include administration by intravenous, intradermal, intramusclar, intramammary, intraperitoneal, intrathecal, retrobulbar, intrapulmonary injection and/or surgical implantation at a particular site.

In a specific embodiment, the medicament is for use by subcutaneous administration. Subcutaneous injections may be performed in short time, in particular when compared to intravenous injection (e.g. approximately 10 minutes for subcutaneous administration compared to about an hour for intravenous infusion). Further, while intravenous administration requires an intravenous access which has to be established by trained personnel, subcutaneous injections may even be performed by the patient himself, e.g. by using automatic injection devices, thus rendering the therapy more convenient for the patient.

Subcutaneous (SC) administration may be performed via a syringe, optionally a prefilled syringe, an injector pen, such as an autoinjector pen, an injection device or an infusion pump or a suitable needleless device. Subcutaneous administration may be performed at a single site of the body or at different sites of the body, e.g. at sites adjacent to each other. Suitable sites for subcutaneous administration are known to the person skilled in the art and include, e.g. the thighs or the upper arms.

Usually subcutaneous injections are limited to a volume of approximately 2 ml or less than 2 ml. This is due to viscoelastic tissue resistance and backpressure generated upon injection as well as pain perceived by the patient. Hence, as only a small volume of the antibody formulation can be provided with a single subcutaneous injection, it can be advantageous to have a lyophilized formulation comprising a high concentration of the anti-CD 20 antibody such as a Veltuzumab antibody which may be reconstituted, in particular in a necessary small volume. This may allow administering high doses of antibodies in a small liquid volume suitable for subcutaneous injection.

In one embodiment, the lyophilized formulation as described herein may be used in the treatment of cancer or a non-malignant disease, optionally inflammatory or autoimmune diseases.

"Cancer" as used herein may relate to any malignant disease involving unregulated cell growth, e.g. Epstein-Barr Virus Infections, Leukemia, Lymphoma, Plasma Cell Neoplasms, Tumor Virus Infections, Immunoproliferative Disorders, Lymphoproliferative Disorders, Paraproteinemias, Herpesviridae Infections, DNA Virus Infections.

In particular, the lyophilized formulation as described herein is useful for the treatment of any CD 20 positive cancers, i.e. cancers showing abnormal proliferation of cells that express CD 20 on the cell surface, in particular T-cells or B-cells. Methods for determining the expression of CD 20 on the cell surface are known in the art and include e.g. FACS or PCR. Exemplary CD 20 positive cancers which can be treated with the lyophilized formulation according to the invention are B cell lymphomas and leukemias.

Lymphomas and leukemias include Burkitt Lymphoma, B-Cell Leukemia, Chronic Lymphocytic B-Cell Leukemia, Acute Lymphoblastic Leukemia, Lymphoid Leukemia, Prolymphocytic Leukemia, Hairy Cell Leukemia, Multiple Myeloma, posttransplant lymphoproliverative disorder (PTLD), HIV-associated Lymphoma, Primary CNS Lymphoma, B-Cell Lymphoma, Marginal Zone B-Cell Lymphoma, Follicular Lymphoma, Diffuse Large B-Cell Lymphoma, Immunoblastic Large-Cell Lymphoma, Mantle-Cell Lymphoma, Non-Hodgkin Lymphoma (e.g. Follicular Lymphoma), Lymphomatoid Granulomatosis, Precursor Cell Lymphoblastic Leukemia-Lymphoma, Waldenstrom Macroglobulinemia, Prolymphocytic Lymphoma, Diffuse Large B-Cell Lymphoma, Immunoblastic Large-Cell Lymphoma, Mantle-Cell Lymphoma, Lymphomatoid Granulomatosis and Precursor Cell Lymphoblastic Leukemia-Lymphoma. Optionally, the CD 20 positive cancer is a disease selected from the group consisting of B-cell non-Hodgkin's Lymphoma, Mantle-Cell Lymphoma, Acute Lymphoblastic Leukemia, Chronic Lymphocytic B-Cell Leukemia, Diffuse Large B-Cell Lymphoma, Burkitt Lymphoma, Follicular Lymphoma, Multiple Myeloma, Marginal Zone B-Cell Lymphoma, posttransplant lymphoproliverative disorder (PTLD), HIV-associated Lymphoma, Waldenstrom Macroglobulinemia, or Waldenstrom Macroglobulinemia. Particularly, the CD 20 positive cancer is a B-cell non-Hodgkin's Lymphoma.

The present invention not only relates to therapeutic treatment of those suffering from any of the above cancers but also to treatment of relapses of these cancers as well as preventive treatment, e.g. treatments of patients being predisposed or susceptible to the disease.

"Non-malignant disease" as used herein relates to any disease not falling under the above definition given for cancers. Non-malignant diseases which may be treated with the lyophilized formulation of the present invention include a disease selected from the group consisting of Autoimmune Diseases, Blood Coagulation Disorders, Blood Platelet Disorders, Blood Protein Disorders, Hematologic Diseases, Hemorrhagic Disorders, Hemostatic Disorders, Lymphatic Diseases, Purpura, Thrombocytopenia, Thrombotic Microangiopathies, Haemostatic Disorders, Vascular Diseases, Rheumatic Diseases, Connective Tissue Diseases, Herpesviridae Infections and DNA Virus Infections. In particular, the lyophilized formulation of the present invention may be used for the treatment of autoimmune diseases.

"Autoimmune diseases" or "autoimmune related conditions" as used herein relate to any disease involving an inappropriate immune response of the body against tissues and/or substances naturally present in the body. Autoimmune diseases or autoimmune related conditions include arthritis (e.g. rheumatoid arthritis, juvenile rheumatoid arthritis, osteoarthritis, psoriatic arthritis), psoriasis, dermatitis (e.g. atopic dermatitis), chronic autoimmune urticaria, polymyositis/dermatomyositis, toxic epidermal necrolysis, systemic scleroderma and sclerosis, inflammatory bowel disease (e.g. Crohn's disease, ulcerative colitis), infant respiratory distress syndrome, adult respiratory distress syndrome (ARDS), meningitis, allergic rhinitis, encephalitis, uveitis, colitis, glomerulonephritis, allergic conditions, eczema, asthma, conditions involving infiltration of T cells and chronic inflammatory responses, atherosclerosis, autoimmune myocarditis, leukocyte adhesion deficiency, systemic lupus erythematosus (SLE), lupus (e.g. nephritis, non-renal, discoid, alopecia), juvenile onset diabetes, multiple sclerosis (e.g. relapse remitting multiple sclerosis, secondary progressive multiple sclerosis, primary progressive multiple sclerosis, progressive relapsing multiple sclerosis and/or clinically isolated syndrome), allergic encephalomyelitis, immune responses associated with acute and delayed hypersensitivity mediated by cytokines and T-lymphocytes, tuberculosis, sarcoidosis, granulomatosis including Wegener's granulomatosis, agranulocytosis, vasculitis (including ANCA), aplastic anemia, Coombs positive anemia, Diamond Blackfan anemia, immune hemolytic anemia including autoimmune hemolytic anemia (AIHA), pernicious anemia, pure red cell aplasia (PRCA), Factor VIII deficiency, hemophilia A, autoimmune neutropenia, pancytopenia, leukopenia, diseases involving leukocyte diapedesis, CNS inflammatory disorders, multiple organ injury syndrome, myasthenia gravis, antigen-antibody complex mediated diseases, anti-glomerular basement membrane disease, anti-phospholipid antibody syndrome, allergic neuritis, Bechet disease, Castleman's syndrome, Goodpasture's Syndrome, Lambert-Eaton Myasthenic Syndrome, Reynaud's syndrome, Sjorgen's syndrome, Stevens-Johnson syndrome, solid organ transplant rejection (including pretreatment for high panel reactive antibody titers, IgA deposit in tissues, etc), graft versus host disease (GVHD), pemphigoid bullous, pemphigus (all including vulgaris, foliatis), autoimmune polyendocrinopathies, Reiter's disease, stiff-man syndrome, giant cell arteritis, immune complex nephritis, IgA nephropathy, IgM polyneuropathies or IgM mediated neuropathy, thrombocytopenia purpura (e.g. idiopathic thrombocytopenic purpura (ITP), thrombotic throbocytopenic purpura (TTP)), autoimmune thrombocytopenia, autoimmune disease of the testis and ovary including autoimune orchitis and oophoritis, primary hypothyroidism; autoimmune endocrine diseases including autoimmune thyroiditis, chronic thyroiditis (Hashimoto's Thyroiditis), subacute thyroiditis, idiopathic hypothyroidism, Addison's disease, Grave's disease, autoimmune polyglandular syndromes (or polyglandular endocrinopathy syndromes), Type I diabetes also referred to as insulin-dependent diabetes mellitus (IDDM) and Sheehan's syndrome; autoimmune hepatitis, Lymphoid interstitial pneumonitis (HIV), bronchiolitis obliterans (non-transplant) vs NSIP, Guillain-Barre'Syndrome, Large Vessel Vasculitis (including Polymyalgia Rheumatica and Giant Cell (Takayasu's) Arteritis), Medium Vessel Vasculitis (including Kawasaki's Disease and Polyarteritis Nodosa), ankylosing spondylitis, Berger's Disease (IgA nephropathy), Rapidly Progressive Glomerulonephritis, Primary biliary cirrhosis, Celiac sprue (gluten enteropathy), Cryoglobulinemia, ALS, coronary artery disease.

In particular, the lyophilized formulation is used for the treatment of a disease selected from the group consisting of arthritis, multiple sclerosis, idiopathic cytopenia, pemphigus, in particular pemphigus vulgaris and/or pemphigus foliatis, thrombocytopenia purpura and/or systemic lupus erythematosum.

In one embodiment, the lyophilized formulation is used for the treatment of arthritis, optionally rheumatoid arthritis.

In a specific embodiment, the lyophilized formulation is used for the treatment of pemphigus, in particular *pemphigus vulgaris* and/or pemphigus foliatis.

In another embodiment, the lyophilized formulation is used for the treatment of thrombocytopenic purpura.

In a further embodiment, the lyophilized formulation is used for the treatment of systemic lupus erythematosum.

In another embodiment, the lyophilized formulation is used for the treatment of idiopathic cytopenia, in particular of idiopathic thrombocytopenic purpura.

In another embodiment, the lyophilized formulation is used for the treatment of multiple sclerosis, optionally for the treatment of relapse remitting multiple sclerosis, secondary progressive multiple sclerosis, primary progressive multiple sclerosis, progressive relapsing multiple sclerosis and/or clinically isolated syndrome.

"Inflammatory disease" as used herein denotes any disease involving acute or chronic inflammation, including inflammatory disorders such as allergies, asthma, cancers and autoimmune diseases.

In one embodiment, lyophilized formulation may be for use in the treatment of a disease selected from the group consisting of leukemia, lymphoma, and/or autoimmune diseases.

In another embodiment, the lyophilized formulation of the invention may be for use in the treatment of a disease selected from the group consisting of Burkitt Lymphoma, Epstein-Barr Virus Infections, B-Cell Leukemia, Chronic Lymphocytic B-Cell Leukemia, Acute Lymphoblastic Leukemia, Lymphoid Leukemia, Prolymphocytic Leukemia, Hairy Cell Leukemia, Multiple Myeloma, B-Cell Lymphoma, Marginal Zone B-Cell Lymphoma, Follicular Lymphoma, Diffuse Large B-Cell Lymphoma, Immunoblastic Large-Cell Lymphoma, Mantle-Cell Lymphoma, Non-Hodgkin Lymphoma, Lymphomatoid Granulomatosis, Plasma Cell Neoplasms, Precursor Cell Lymphoblastic Leukemia-Lymphoma, Tumor Virus Infections, Waldenstrom Macroglobulinemia, Immunoproliferative Disorders, Prolymphocytic Lymphoma, Diffuse Large B-Cell Lymphoma, Immunoblastic Large-Cell Lymphoma, Mantle-Cell Lymphoma, Lymphomatoid Granulomatosis, Lymphoproliferative Disorders, Paraproteinemias, Precursor Cell Lymphoblastic Leukemia-Lymphoma, multiple sclerosis, optionally relapse remitting multiple sclerosis, secondary progressive multiple sclerosis, primary progressive multiple sclerosis, progressive relapsing multiple sclerosis and/or clinically isolated syndrome, idiopathic cytopenia, Thrombocytopenic Purpura, Idiopathic Thrombocytopenic Purpura, Blood Coagulation Disorders, Blood Platelet Disorders, Blood Protein Disorders, Hematologic Diseases, Hemorrhagic Disorders, Hemostatic Disorders, Lymphatic Diseases, Purpura, Thrombocytopenia, Thrombotic Microangiopathies, Haemostatic Disorders, Vascular Diseases, Rheumatoid Arthritis, Rheumatic Diseases, Connective Tissue Diseases, Pemphigus, systemic lupus erythematosum, multiple sclerosis, Herpesviridae Infections, and/or DNA Virus Infections.

The lyophilized formulation of the invention may be provided in unit dosage form (e.g. in containers, bottles, vials or syringes) or in multiple dosage form (e.g. in multi-dose containers). Suitable containers and materials for providing such containers (e.g. glass) are known to the person skilled in the art. The container holding the lyophilized formulation may only comprise the lyophilized formulation or may further comprise a second compartment holding the diluents for reconstituting the lyophilized formulation.

The lyophilized formulation of the invention may be administered alone or in combination with any further therapeutic agent considered suitable by the person skilled in the art for the treatment of any of the above mentioned diseases. The further therapeutic agent may be administered separately, concurrently or sequentially with the formulation according to the present invention. Examples of such further therapeutic agents are e.g. cytotoxic agents, anti-angiogenic agents, corticosteroids, antibodies, chemotherapeutics, hormones, anti-inflammatory drugs and immunomodulators.

Another aspect of the present invention relates to a method of treating a patient comprising the following steps:
(i) providing a lyophilized formulation of an anti-CD20 antibody according to the described herein,
(ii) reconstituting the lyophilized formulation, and
(iii) administering the reconstituted formulation to a patient.

It is understood, that step (i) of the method of treating a patient may include any steps described herein with respect to the method for providing a lyophilized formulation of an anti-CD 20 antibody. In one embodiment, the lyophilized formulation provided in step (i) of the method of treating a patient, is a lyophilized formulation of Veltuzumab or a fragment thereof.

In step (ii) of the method of treating a patient, the lyophilized formulation may be reconstituted with any reconstitution medium as described herein considered suitable by the person skilled in the art.

Step (iii) of the method of treating a patient may, in one embodiment, relate to parenteral administration, e.g. subcutaneous, intravenous, intradermal, intramuscular, intramammary, intraperitoneal, intrathecal, retrobulbar, intrapulmonary administration and/or surgical implantation at a particular site. In one embodiment of the method of treating a patient, step (iii) relates to subcutaneous administration of the reconstituted formulation. However, any mode and method of administration described herein may also be used in step (iii) of the method of treatment described herein.

The patient treated by the method described herein may be suffering from one or more of the diseases and/or conditions described herein. In one embodiment of the method of treating a patient described herein, the patient is suffering from cancer and/or a non-malignant disease, optionally an autoimmune disease. In one embodiment, the patient to be treated by the method of treatment described herein is a patient suffering from rheumatoid arthritis, systemic lupus erythematosum, idiopathic cytopenia, thrombocytopenia purpura and/or pemphigus, in particular from systemic lupus erythematosum.

The invention is further described in the following examples which are solely for the purpose of illustrating specific embodiments of the invention, and are also not to be construed as limiting the scope of the invention in any way.

EXAMPLES

Example 1

Influence of the Residual Moisture Content on Tg, Reconstitution and Aggregation In order to determine whether there is a level of residual moisture in the lyophilized formulation which improves stability during storage, the influence of residual moisture on the glass transition temperature (Tg), the reconstitution time of the lyophilized formulation and on aggregation was determined.

For this, a composition comprising the following ingredients was subjected to lyophilization:

| | |
|---|---|
| Veltuzumab | 50.0 mg/g |
| Sucrose | 41.0 mg/g (~120 mM) |
| L-Histidine | 0.270 mg/g |
| L-HistidineHCl*H$_2$O | 1.733 mg/g (~10 mM total histidine) |
| Polysorbate 20 | 0.10 mg/g |
| pH | 5.5 ± 0.2 |
| Osmolality | 150 mOsm/kg |

The solution was sterile filtered, filled into vials, partly stoppered with lyophilization stoppers and put into a freeze dryer. In order to obtain different residual moistures in the lyophilizate, the drying temperature in the second drying step was varied, i.e. the samples were subjected to 0° C., 20° C. or 40° C. for four hours in the second drying step. The lyophilization process performed is described in Table 1, depicting as an exemplary temperature 20° C. in the secondary drying step.

TABLE 1

Lyophilization process

| Step | Time/Rate | Temperature (° C.) | Pressure (mbar) |
|---|---|---|---|
| 1, loading | n.a. | RT | 1000 |
| 2, ramp to freezing 1 | 1° C./min | To −50 | 1000 |
| 3, freezing 1 | 1 h | −50 | 1000 |
| 4, ramp to annealing | 1° C./min | To −15 | 1000 |
| 5, annealing | 4 h | −15 | 1000 |
| 6, ramp to freezing 2 | 1° C./min | To −50 | 1000 |
| 7, freezing 2 | 2 h | −50 | 1000 |
| 8, ramp to preevac. | 1° C./min | To −30 | 1000 |
| 9, preevacuation | 15 min | −30 | 0.1 |
| 10, ramp to primary drying | 1° C./min | To −20 | 0.1 |
| 11, primary drying | 48 h | −20 | 0.1 |
| 12, ramp to secondary drying | 0.1° C./min | To +20 | 0.1 |
| 13, secondary drying | 4 h | +20 | 0.1 |

Total duration of the cycle: approx. 68.5 h

The samples derived from said process having a residual moisture content of 2.02%, 1.25% and 0.80% were subsequently stored at 40° C. for 12 weeks.

The residual moisture content was determined by Karl Fischer titration with biamperometric endpoint detection in a KF titrator 784 Titrino (Metrohm) with ultra turrax. For this, the vial was opened and the lyophilisate was broken with a spatula. Subsequently, 200 mg of the powder were transferred into the receiver. The lyophilisate was homogenized with the ultra-turrax at 8000 rpm for 30 seconds. Then, the powder was titrated with an adjusted Karl-Fischer reagent (e.g. Hydranal Composite 5 obtained from Riedel de Haen).

Furthermore, the glas transition temperature was determined by differential scanning calometry before storage, whereby the following parameters were used:
System: TA Instruments Q 2000
Pan type: T$_{zero}$ Aluminium hermetic
Equilibration at −20° C. for 5 minutes
Modulation ±0.6° C. every 90 seconds
Ramp 2.5° C./min to 160° C.

Figure 2:
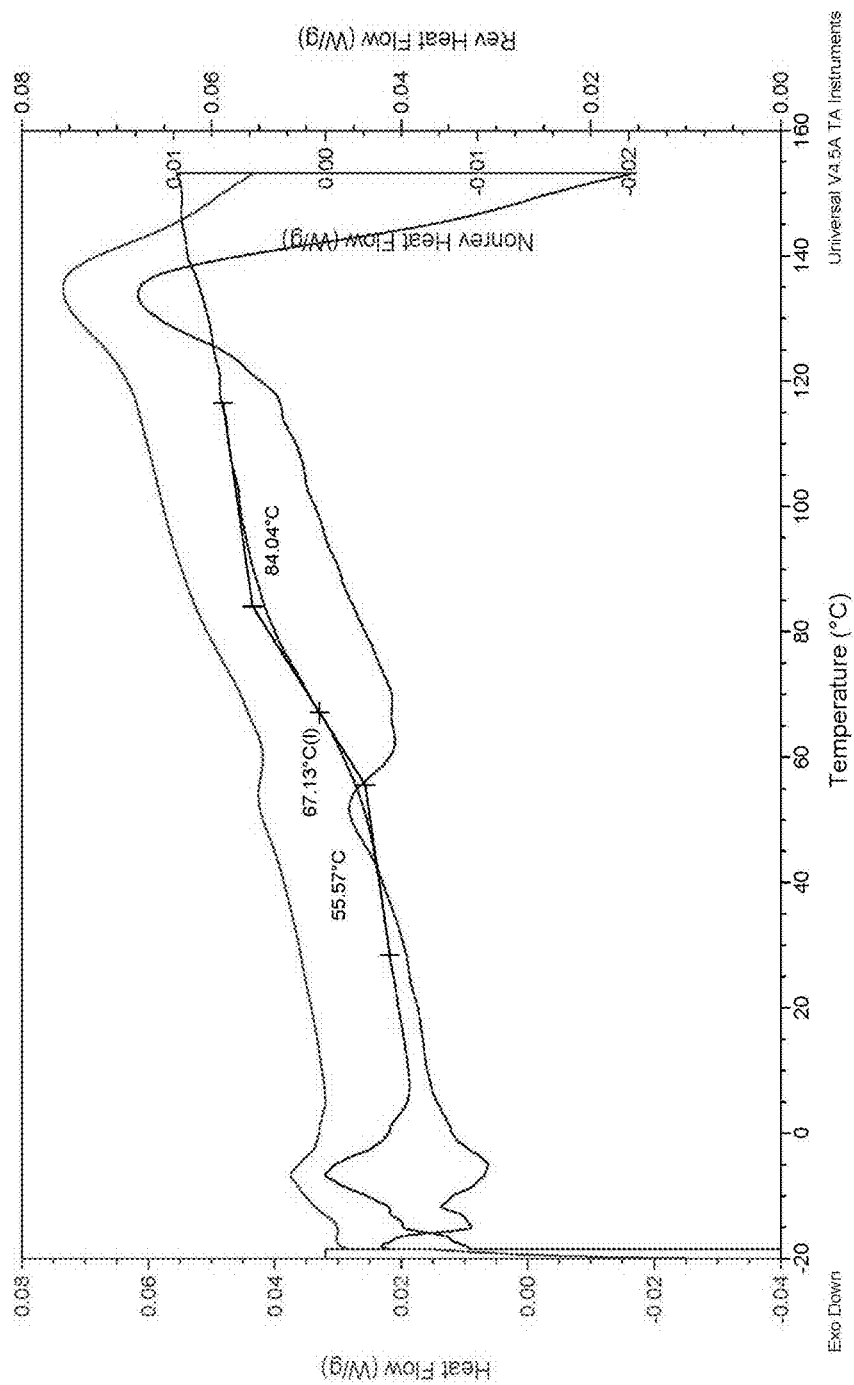
FIG. 2 depicts a DSC analysis of one sample which was prepared according to the process as described in Example 1 and wherein the secondary drying step was performed at 20° C. The upper and the lower line show the heating and the cooling curve. The cross shows the midpoint of glass transition.
Figure 3:
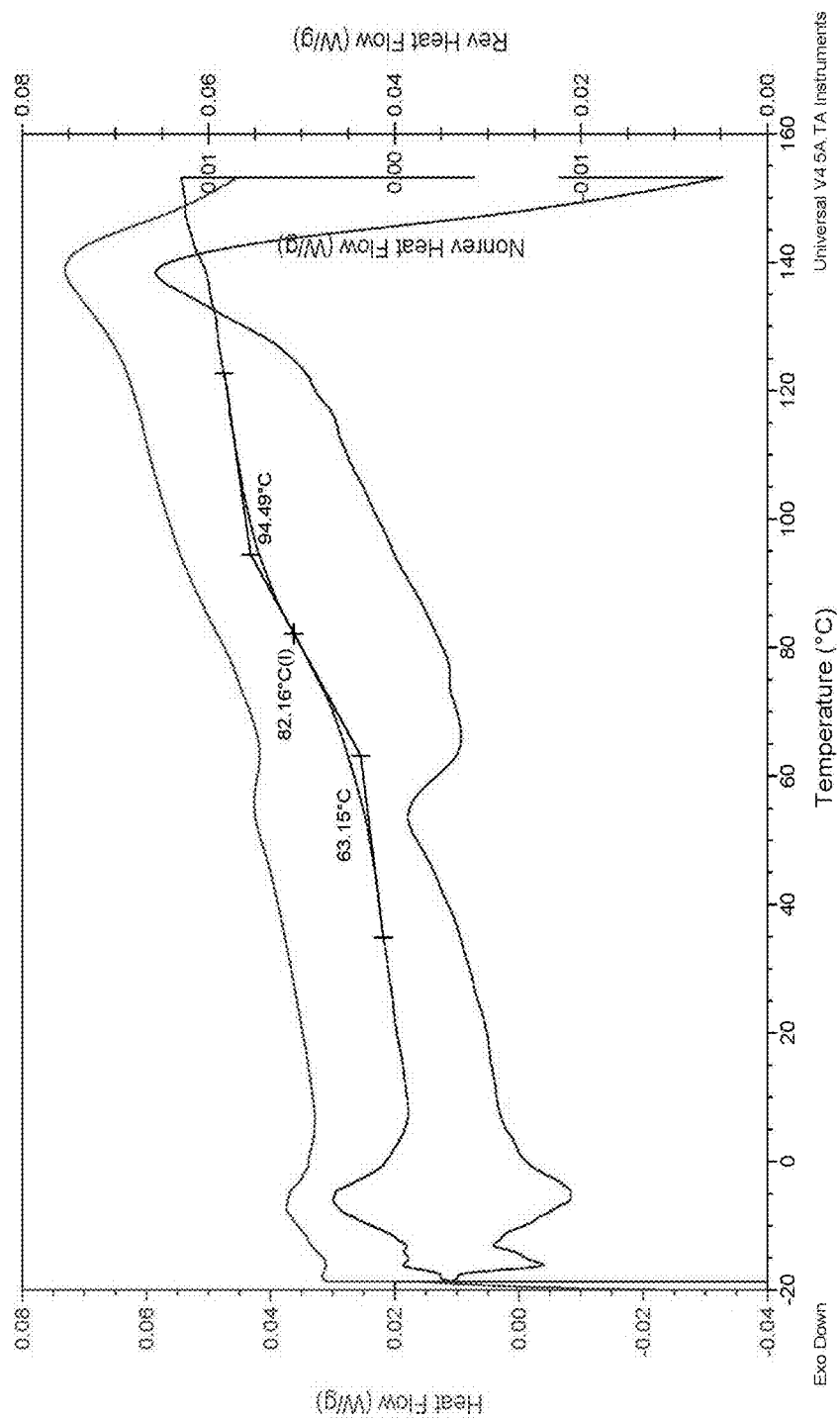
FIG. 3 depicts a DSC analysis of one sample which was prepared according to the process as described in Example 1 and wherein the secondary drying step was performed at 40° C. The upper and the lower line show the heating and the cooling curve. The cross shows the midpoint of glass transition.
Figure 4:
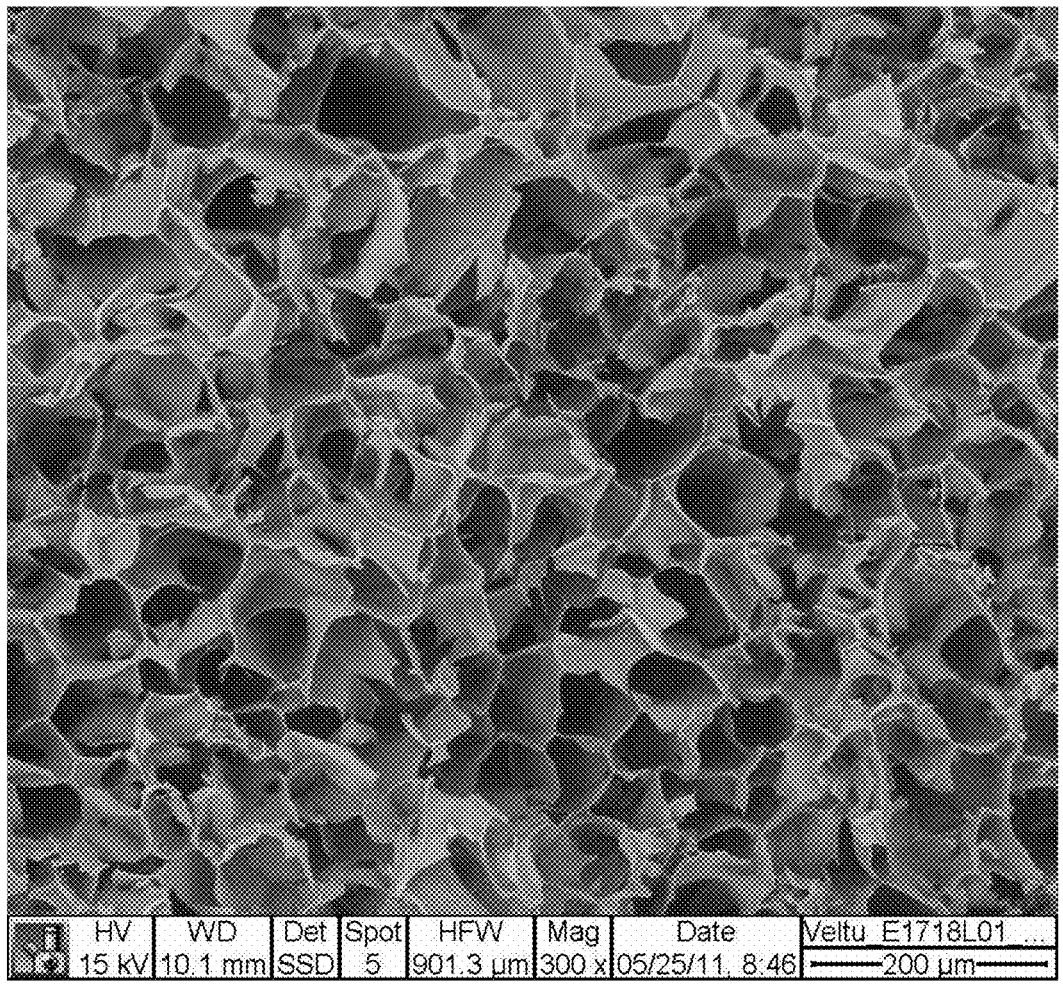
FIG. 4 shows a REM image (300×) of the morphology of the middle outer part of a Veltuzumab lyophilisate obtained with the freeze-drying process according to Example 3.
Figure 5:
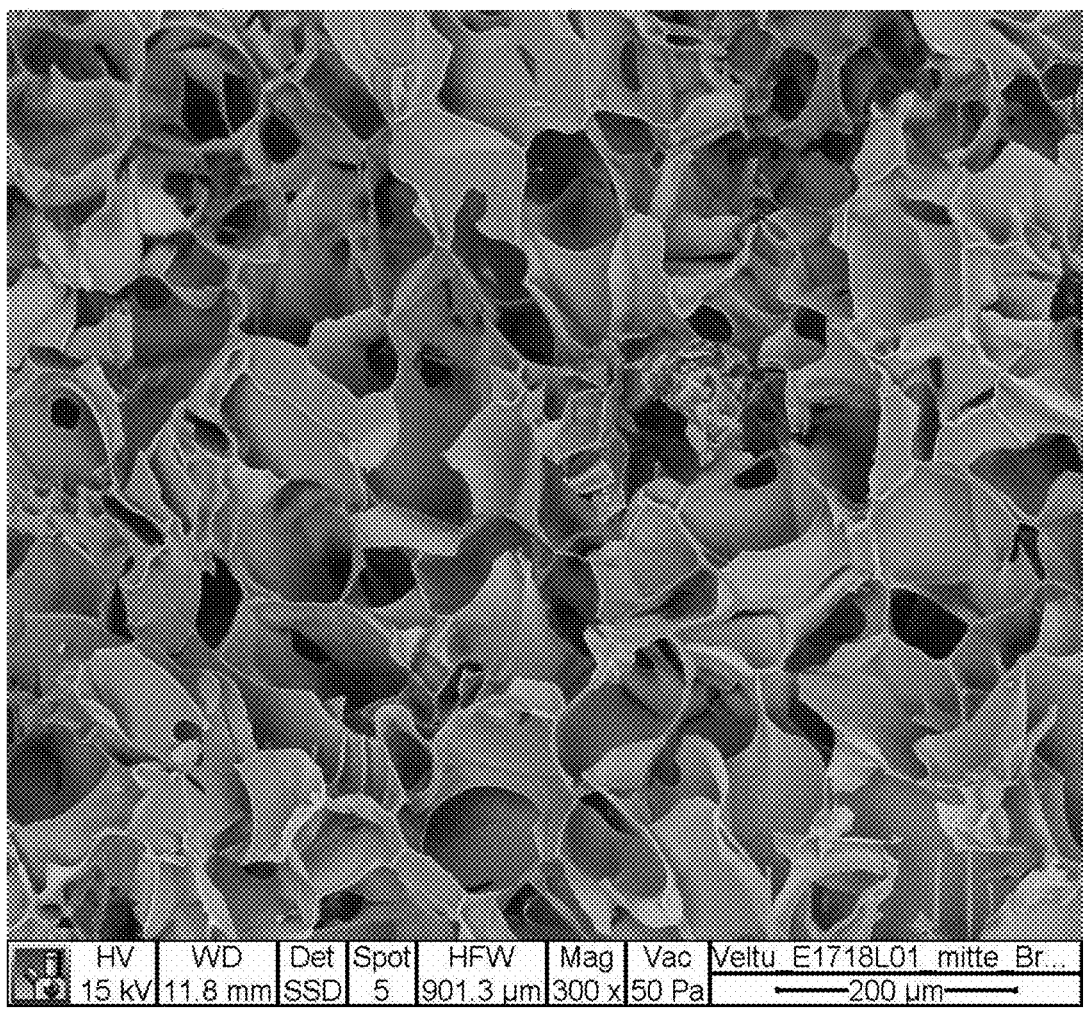
FIG. 5 shows a REM image (300×) of the morphology of the middle inner part of a Veltuzumab lyophilisate obtained with the freeze-drying process according to Example 3. As can be derived from FIGS. 4 and 5, the morphology and pore structure does not significantly differ in the inner and outer part of the lyophilisate.

FIGS. 1-3 show exemplary DSC curves of one of the samples subjected to 0° C., 20° C. and 40° C., respectively.

Also, aggregation was determined by size exclusion chromatography before and after storage, whereby the starting value for aggregation was 1.1% in all samples. The aggregation value after storeage is depicted in Table 2 below.

Additionally the reconstitution time of the lyophilizates obtained was determined after storage.

In Table 2, the values obtained for the glass transition temperature, the reconstitution behavior and the aggregation in the samples having a different residual moisture content are summarized.

TABLE 2

Tg, reconstitution and aggregation after storage (mean value of two samples)

| Secondary drying (° C.) | Tg (° C.) | Residual moisture (%) | Reconstitution time (min) | Aggregation (%) |
|---|---|---|---|---|
| 0 | 61.6 | 2.02 | 10 to 15 | 2.15 |
| 20 | 67.3 | 1.25 | 10 to 15 | 2.51 |
| 40 | 76.2 | 0.80 | 10 to 20 | 2.67 |

As can be derived from the above Table 2, an increase in residual moisture content decreases the level of aggregation after storage, thus providing a more stable lyophilisate.

Example 2

Freeze-Drying Process

Furthermore, the freeze-drying process shown in Table 3 was developed, allowing to produce lyophilisates of Veltuzumab exhibiting a residual moisture content between 1.5 and 2.5% throughout the whole lot.

TABLE 3

Freeze-drying process

| Step | Description | Shelf Temperature (° C.) | Duration (min) | Pressure (mbar) |
|---|---|---|---|---|
| 1 | Loading | +20 | — | atm |
| 2 | Ramp phase | −5 | 25 | atm |
| 3 | Equilibration phase | −5 | 30 | atm |
| 4 | Ramp phase | −40 | 35 | atm |
| 5 | Freezing | −40 | 120 | atm |
| 6 | Evacuation | −40 | 15 | 0.19 |
| 7 | Ramp phase | +8 | 48 | 0.19 |
| 8 | Main drying I | +8 | 2166 | 0.19 |
| 9 | Ramp phase | +5 | 3 | 0.19 |
| 10 | Main drying II | +5 | 260 | 0.19 |
| 11 | Venting Stoppering | +5 | 15 | 850 |

Total duration of steps 2 to 10 is 45 hours

This freeze-drying process does not involve a secondary drying step at elevated temperatures compared to the temperatures used in the first drying step.

The characteristics of the lyophilizate obtained by the above-described process were determined. The residual moisture content was determined from eight individual vials distributed in different positions (i.e. edge and center vials) on the shelves. As can be derived from Table 4, a lyophilisate having the desired residual moisture content and stable upon storage at 40° C. could be obtained.

TABLE 4

Characteristics of lyophilizate obtained by the freeze-drying process according to Table 3

| Parameter | Value |
|---|---|
| Residual moisture | 1.5 to 1.8% |
| Glass transition temperature | 57° C. |
| pH | 5.51 |
| Reconstitution | 10 min |
| Extractable volume | 2.50 mL |
| Concentration after reconstitution | 122 mg/mL |
| Aggregates after 6 weeks storage at 40° C. | Increase from 0.56 to 0.92 |

Example 3

Preparation and Reconstitution of a Lyophilized Formulation

A pre-lyophilization composition having the following components was subjected to lyophilization.

| | |
|---|---|
| Veltuzumab | 50.0 mg/g |
| Sucrose | 41.0 mg/g (~120 mM) |
| L-Histidine | 0.270 mg/g |
| L-HistidineHCl*H$_2$O | 1.733 mg/g (~10 mM total histidine) |
| Polysorbate 20 | 0.10 mg/g |
| pH | 5.5 ± 0.2 |
| Osmolality | 150 mOsm/kg |

7.10 g of the pre-lyophilization composition were filled in vials (10 R vials type 1, Schott) and subjected to the lyophilization process described in Table 3.

The lyophilitate was subsequently stored for 12 months at +5° C. in stoppered glass vials. From the results shown in Table 3 it can be derived that the so-obtained lyophilizate is stable during storage at 5° C. at +5° C.

TABLE 5

Results after 1, 3, 6, 9, 12 and 18 months storage at +5° C.

| | Test method | 0 months | 1 month | 3 months | 6 months | 9 months | 12 months | 18 months |
|---|---|---|---|---|---|---|---|---|
| Residual moisture % | | 1.9 | 2.0 | 2.4 | 1.9 | 1.9 | 2.3 | 2.4 |
| Upon reconstruction | | | | | | | | |
| Visible particles | Solution essentially free of foreign particles | Pass | Pass | Pass | Pass | Pass | Pass | Pass |
| Particulate contamination ≥10 μm | | 69 | 40 | 21 | 40 | 30 | 24 | 50 |
| Particulate contamination ≥25 μm | | 26 | 8 | 2 | 21 | 19 | 8 | 27 |

TABLE 5-continued

Results after 1, 3, 6, 9, 12 and 18 months storage at +5° C.

| Test method | | 0 months | 1 month | 3 months | 6 months | 9 months | 12 months | 18 months |
|---|---|---|---|---|---|---|---|---|
| pH | | 5.5 | 5.5 | 5.5 | 5.5 | 5.5 | 5.5 | 5.5 |
| Osmolality (mOsmol/kg) | | 506 | 512 | 496 | 493 | 514 | 493 | 497 |
| UV-Scan(mg/mL) | | 127.6 | 128.7 | 129.3 | 128.9 | 122.3 | 127.1 | 127.9 |
| CEX | Report result [%] APG: | 14 | 13 | 14 | 15 | 15 | 15 | 15 |
| | Main Peak | 69 | 72 | 71 | 68 | 68 | 69 | 70 |
| | BPG | 17 | 14 | 15 | 17 | 17 | 15 | 15 |
| CGE reduced Σ heavy and light chains % | | 97.7 | 97.5 | 97.7 | 97.8 | 97.7 | 97.8 | 98.0 |
| CGE non reduced Main peak % | | 97.1 | 97.3 | 97.2 | 97.3 | 97.3 | 97.2 | 97.0 |
| HP-SEC Monomer % | | 100 | 100 | 100 | 100 | 100 | 100 | 100 |
| CDC Bioassay | | 114 | 109 | 107 | 109 | 109 | 108 | 107 |

CEX Cationic Exchange Chromatography,
APG acidic peak group,
BPG basic peak group,
CGE Capillary Gel Electrophoresis,
HP-SEC S Exclusion - High Performance Liquid Chromatography,
CDC Complement-Dependent Cytotoxicity After reconstitution (reconstitution time five minutes until the lyophilisate was completely dissolved) of the lyophilizate with 2.2 mL of water for injection the following composition is obtained:

| Veltuzumab | 133 mg/mL |
|---|---|
| Sucrose | 109 mg/mL (~320 mM) |

-continued

| L-Histidine | 0.718 mg/mL |
|---|---|
| L-HistidineHCl*H$_2$O | 4.610 mg/g (~27 mM total histidine) |
| Polysorbate 20 | 0.27 mg/mL |
| pH | 5.5 ± 0.2 |
| Osmolality | ~450 mOsm/kg |

The invention claimed is:

1. A method for providing a lyophilized formulation of an anti-CD 20 antibody, comprising the steps of:
   I) providing a solution comprising the anti-CD 20 antibody,
   II) freezing the antibody solution and,
   III) subjecting the antibody solution to at least one drying step at a shelf temperature of −10° C. to 30° C., in order to obtain the lyophilized formulation, wherein the lyophilized formulation has a residual moisture content in the range of about 1.5% to 1.8%.

2. The method according to claim 1, wherein the antibody solution is subjected to one drying step.

3. The method according to claim 1, further including subjecting the antibody solution to a second drying step, wherein the shelf temperature used in the second drying step is lower than the shelf temperature used in the first drying step.

4. The method according to claim 3, wherein the shelf temperature used in the second drying step is at least 2° C. lower, optionally at least 3° C. lower than the shelf temperature used in the first drying step.

5. The method according to claim 1, wherein the shelf temperature used in the first drying step is 8° C. and/or the shelf temperature used in the second drying step is 5° C.

6. The method according to claim 1, wherein the solution provided in step (I) comprises a buffering agent, optionally a buffering agent comprising histidine or phosphate.

7. The method according to claim 1, wherein the solution provided in step (I) comprises a tonicity modifying agent, optionally sucrose.

8. The method according to claim 1, wherein the solution provided in step (I) comprises a surfactant, optionally a nonionic surfactant.

9. The method according to claim 1, wherein the solution provided in step (I) has a pH value in the range of 5.0 to 7.0, optionally a pH value of 5.5±0.3.

10. The method according to claim 1, wherein the solution provided in step (I) comprises
   a) at least 40 mg/g anti-CD 20 antibody,
   b) 5-15 mM histidine,
   c) 100-150 mM sucrose,
   d) 0.05-0.5 mg/g polysorbate 20; and
   wherein the solution provided in step (I) has a pH value of 5.5±0.3.

11. The method according to claim 1, wherein the anti-CD 20 antibody is Veltuzumab or a fragment thereof.

12. A method for providing a liquid formulation of an anti-CD 20 antibody, comprising providing a lyophilized formulation according to the method of claim 1 and subsequently performing a step IV) of reconstituting the lyophilized formulation.

13. The method according to claim 12, wherein the liquid formulation obtained in step IV) comprises
   a) at least 80 mg/mL anti-CD 20 antibody,
   b) 10-40 mM buffering agent, optionally a buffering agent comprising histidine,
   c) 200-400 mM tonicity modifying agent, optionally sucrose,
   d) 0.2-0.5 mg/mL surfactant, optionally polysorbate 20; and
   has a pH value of 5.5±0.3.

14. A lyophilized formulation of an anti-CD 20 antibody, obtained by a method comprising the steps of:
   I) providing a solution comprising the anti-CD 20 antibody,
   II) freezing the antibody solution, and
   III) subjecting the antibody solution to at least two drying steps, with a first drying step at a shelf temperature of −10° C. to 30° C., and a second drying step,
   wherein the anti-CD 20 antibody is veltuzumab or an antigen-binding fragment thereof, wherein the first drying step and the second drying step each changes the temperature to the shelf temperature at a rate of 1° C. per minute, wherein the second drying step is at a shelf temperature lower than the shelf temperature of the first drying step, wherein the formulation has a residual moisture content in the range of about 1.5% to 1.8%, and wherein the formulation exhibits increased stability and reduced tendency to form aggregates during storage, as determined by measurement of particulate contamination, or by HP-SEC (high performance size-exclusion chromatography) monomer %.

15. The lyophilized formulation according to claim 14, further comprising a buffering agent, optionally a buffering agent comprising histidine or phosphate.

16. The lyophilized formulation according to claim 14, further comprising a tonicity modifying agent, optionally sucrose.

17. The lyophilized formulation according to claim 14, further comprising a surfactant, optionally a nonionic surfactant.

18. The lyophilized formulation of claim 14, wherein the residual moisture content is about 1.5%.

19. The lyophilized formulation according to claim 14, wherein the shelf temperature of the second drying step is at least 2° C. lower than the shelf temperature of the first drying step.

20. A reconstituted formulation of an anti-CD 20 antibody, obtained by a method comprising reconstituting the lyophilized formulation of claim 14.

21. A reconstituted formulation of an anti-CD 20 antibody, obtained by a method comprising reconstituting the lyophilized formulation of claim 19.

22. A medicament comprising the reconstituted formulation according to claim 21.

23. The medicament according to claim 22, wherein the medicament is formulated for parenteral administration, optionally for subcutaneous administration.

24. The lyophilized formulation according to claim 19, wherein the shelf temperature of the first drying step is about 8° C., and the shelf temperature of the second drying step is about 5° C.

25. A medicament comprising the reconstituted formulation according to claim 20.

26. The medicament according to claim 25, wherein the medicament is formulated for parenteral administration, optionally for subcutaneous administration.

27. The reconstituted formulation of claim 21, wherein the lyophilized formulation of step III) has a residual moisture content of about 1.5%.

28. The medicament according to claim 25, wherein the lyophilized formulation has a residual moisture content of about 1.5%.

29. The medicament according to claim 26, where in the lyophilized formulation has a residual moisture content of about 1.5%.

* * * * *

```
                        SEQUENCE LISTING

<160> NUMBER OF SEQ ID NOS: 2

<210> SEQ ID NO 1
<211> LENGTH: 451
<212> TYPE: PRT
<213> ORGANISM: Artificial Sequence
<220> FEATURE:
<223> OTHER INFORMATION: Veltuzumab antibody heavy chain

<400> SEQUENCE: 1

Gln Val Gln Leu Gln Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30

Asn Met His Trp Val Lys Gln Ala Pro Gly Gln Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Glu Ser Thr Asn Thr Ala Tyr
65                  70                  75                  80

Met Glu Leu Ser Ser Leu Arg Ser Glu Asp Thr Ala Phe Tyr Tyr Cys
                85                  90                  95

Ala Arg Ser Thr Tyr Tyr Gly Gly Asp Trp Tyr Phe Asn Val Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140
```

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Thr Val
        180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Arg Val Glu Pro Lys Ser Cys
        210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 2
<211> LENGTH: 213
<212> TYPE: PRT
<213> ORGANISM: Artificial Sequence
<220> FEATURE:
<223> OTHER INFORMATION: Veltuzumab antibody light chain

<400> SEQUENCE: 2

Asp Ile Gln Leu Thr Gln Ser Pro Ser Ser Leu Ser Ala Ser Val Gly
1               5                   10                  15

Asp Arg Val Thr Met Thr Cys Arg Ala Ser Ser Ser Val Ser Tyr Ile
            20                  25                  30

His Trp Phe Gln Gln Lys Pro Gly Lys Ala Pro Lys Pro Trp Ile Tyr
        35                  40                  45

```
Ala Thr Ser Asn Leu Ala Ser Gly Val Pro Val Arg Phe Ser Gly Ser
     50                  55                  60

Gly Ser Gly Thr Asp Tyr Thr Phe Thr Ile Ser Ser Leu Gln Pro Glu
 65              70                  75                      80

Asp Ile Ala Thr Tyr Tyr Cys Gln Gln Trp Thr Ser Asn Pro Pro Thr
                 85              90                   95

Phe Gly Gly Gly Thr Lys Leu Glu Ile Lys Arg Thr Val Ala Ala Pro
             100             105                     110

Ser Val Phe Ile Phe Pro Pro Ser Asp Glu Gln Leu Lys Ser Gly Thr
         115             120                 125

Ala Ser Val Val Cys Leu Leu Asn Asn Phe Tyr Pro Arg Glu Ala Lys
     130             135                 140

Val Gln Trp Lys Val Asp Asn Ala Leu Gln Ser Gly Asn Ser Gln Glu
145             150                 155                     160

Ser Val Thr Glu Gln Asp Ser Lys Asp Ser Thr Tyr Ser Leu Ser Ser
             165             170                     175

Thr Leu Thr Leu Ser Lys Ala Asp Tyr Glu Lys His Lys Val Tyr Ala
             180             185                     190

Cys Glu Val Thr His Gln Gly Leu Ser Ser Pro Val Thr Lys Ser Phe
         195             200                 205

Asn Arg Gly Glu Cys
             210
```